United States Patent
Goldfarb et al.

(10) Patent No.: US 10,716,629 B2
(45) Date of Patent: *Jul. 21, 2020

(54) METHODS AND DEVICES FOR FACILITATING VISUALIZATION IN A SURGICAL ENVIRONMENT

(71) Applicant: Acclarent, Inc., Irvine, CA (US)

(72) Inventors: Eric Goldfarb, Belmont, CA (US); John H. Morriss, Emerald Hills, CA (US); John Y. Chang, Los Altos, CA (US); William M. Facteau, Atherton, CA (US)

(73) Assignee: Acclarent, Inc., Irvine, CA (US)

( * ) Notice: Subject to any disclaimer, the term of this patent is extended or adjusted under 35 U.S.C. 154(b) by 599 days.

This patent is subject to a terminal disclaimer.

(21) Appl. No.: 15/443,294

(22) Filed: Feb. 27, 2017

(65) Prior Publication Data

US 2017/0231698 A1 Aug. 17, 2017

Related U.S. Application Data

(63) Continuation of application No. 12/479,332, filed on Jun. 5, 2009, now Pat. No. 9,603,506, which is a
(Continued)

(51) Int. Cl.
*A61B 34/20* (2016.01)
*A61B 1/07* (2006.01)
(Continued)

(52) U.S. Cl.
CPC .......... *A61B 34/20* (2016.02); *A61B 1/00126* (2013.01); *A61B 1/063* (2013.01);
(Continued)

(58) Field of Classification Search
CPC .......... A61B 34/20; A61B 1/07; A61B 5/6851; A61B 2562/228; G02B 23/2469;
(Continued)

(56) References Cited

U.S. PATENT DOCUMENTS

| 446,173 A | 2/1891 | Hancock |
|---|---|---|
| 504,424 A | 9/1893 | De Pezzer |

(Continued)

FOREIGN PATENT DOCUMENTS

| CA | 2013323 | 9/1990 |
|---|---|---|
| CH | 668188 | 12/1988 |

(Continued)

OTHER PUBLICATIONS

European Communication dated Oct. 12, 2018 for Application No. 078361102, 6 pages.

(Continued)

*Primary Examiner* — Sean P Dougherty
(74) *Attorney, Agent, or Firm* — Frost Brown Todd LLC

(57) ABSTRACT

Devices and methods for visually confirming the positioning of a distal end portion of an illuminating device placed within a patient include inserting a distal end portion of an illuminating device internally into a patient, emitting light from the distal end portion of the illuminating device, observing transillumination resulting from the light emitted from the distal end portion of the illuminating device that occurs on an external surface of the patient, and correlating the location of the observed transillumination on the external surface of the patient with an internal location of the patient that underlies the location of observed transillumination, to confirm positioning of the distal end portion of the illuminating device.

20 Claims, 10 Drawing Sheets

Related U.S. Application Data continuation of application No. 11/522,497, filed on Sep. 15, 2006, now Pat. No. 7,559,925.

(51) Int. Cl.

| | | |
|---|---|---|
| *G02B 6/26* | (2006.01) | |
| *G02B 6/24* | (2006.01) | |
| *A61B 1/233* | (2006.01) | |
| *A61B 5/00* | (2006.01) | |
| *A61M 25/09* | (2006.01) | |
| *F21V 8/00* | (2006.01) | |
| *A61B 1/00* | (2006.01) | |
| *G02B 6/42* | (2006.01) | |
| *A61B 1/06* | (2006.01) | |
| *A61B 5/06* | (2006.01) | |
| *A61B 17/24* | (2006.01) | |
| *A61M 29/02* | (2006.01) | |
| *G02B 23/24* | (2006.01) | |
| *G02B 6/122* | (2006.01) | |
| *G02B 6/125* | (2006.01) | |
| *A61B 18/22* | (2006.01) | |
| *A61M 25/01* | (2006.01) | |
| *G02B 6/04* | (2006.01) | |
| *A61B 90/30* | (2016.01) | |

(52) U.S. Cl.
CPC ............ *A61B 1/0684* (2013.01); *A61B 1/07* (2013.01); *A61B 1/233* (2013.01); *A61B 5/0084* (2013.01); *A61B 5/062* (2013.01); *A61B 5/6851* (2013.01); *A61B 17/24* (2013.01); *A61M 25/09* (2013.01); *A61M 29/02* (2013.01); *G02B 6/0006* (2013.01); *G02B 6/0008* (2013.01); *G02B 6/241* (2013.01); *G02B 6/262* (2013.01); *G02B 6/4292* (2013.01); *G02B 23/2469* (2013.01); *A61B 5/061* (2013.01); *A61B 5/064* (2013.01); *A61B 2017/246* (2013.01); *A61B 2018/2222* (2013.01); *A61B 2018/2244* (2013.01); *A61B 2034/2055* (2016.02); *A61B 2090/306* (2016.02); *A61B 2217/005* (2013.01); *A61B 2562/228* (2013.01); *A61M 25/0105* (2013.01); *A61M 2025/0166* (2013.01); *A61M 2025/09008* (2013.01); *A61M 2025/09083* (2013.01); *A61M 2025/09125* (2013.01); *A61M 2025/09166* (2013.01); *A61M 2025/09175* (2013.01); *A61M 2029/025* (2013.01); *G02B 6/04* (2013.01); *G02B 6/125* (2013.01); *G02B 6/1228* (2013.01)

(58) Field of Classification Search
CPC .... G02B 6/0008; G02B 6/4292; A61M 25/09; A61M 2025/09008; A61M 2025/0166
See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,889,776 A | 6/1975 | Postma |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,192,317 A | 3/1980 | Munnerlyn |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,306,715 A | 12/1981 | Sutherland |
| 4,312,353 A | 1/1982 | Shahbabian |
| 4,338,941 A | 7/1982 | Payton |
| D269,204 S | 5/1983 | Trepp |
| 4,388,941 A | 6/1983 | Reidhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |

(56) References Cited

U.S. PATENT DOCUMENTS

| | | |
|---|---|---|
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,705,801 A | 11/1987 | Martin et al. |
| 4,708,434 A | 11/1987 | Tsuno |
| 4,708,834 A | 11/1987 | Cohen et al. |
| 4,723,936 A | 2/1988 | Buchbinder et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,324,306 A | 6/1994 | Makower et al. |
| 5,333,620 A | 8/1994 | Moutafis et al. |
| 5,334,143 A | 8/1994 | Carroll |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |

(56) References Cited

U.S. PATENT DOCUMENTS

| | | |
|---|---|---|
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | von Hoffmann |
| 5,882,333 A | 3/1999 | Schaer et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |

(56) References Cited

U.S. PATENT DOCUMENTS

| | | |
|---|---|---|
| 5,984,945 A | 11/1999 | Sirhan |
| 5,985,307 A | 11/1999 | Hanson et al. |
| 5,987,344 A | 11/1999 | West |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,306,105 B1 | 10/2001 | Rooney et al. |
| 6,306,124 B1 | 10/2001 | Jones et al. |
| 6,308,092 B1 | 10/2001 | Hoyns |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,393,312 B1 | 5/2002 | Hoyns |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,408 B1 | 10/2002 | Nolan |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,573,984 B2 | 6/2003 | Jung et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |

(56) References Cited

U.S. PATENT DOCUMENTS

| | | |
|---|---|---|
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,623,172 B1 | 9/2003 | De Jong et al. |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,044,964 B2 | 5/2006 | Jang et al. |
| 7,048,711 B2 | 5/2006 | Rosenman et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,077,836 B2 | 7/2006 | Lary et al. |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,474,820 B2 | 1/2009 | Vayser et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |

(56) References Cited

U.S. PATENT DOCUMENTS

| | | | |
|---|---|---|---|
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Roßner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,439,687 B1 | 5/2013 | Morriss et al. |
| 8,535,707 B2 | 9/2013 | Arensdorf et al. |
| 8,585,728 B2 | 11/2013 | Keith et al. |
| 8,585,753 B2 | 11/2013 | Scanlon et al. |
| 8,608,360 B2 | 12/2013 | Nath |
| 8,715,169 B2 | 5/2014 | Chang et al. |
| 8,718,786 B2 | 5/2014 | Shalev |
| 8,740,929 B2 | 6/2014 | Gopferich et al. |
| 8,747,389 B2 | 6/2014 | Goldfarb et al. |
| 8,764,729 B2 | 7/2014 | Muni et al. |
| 8,828,041 B2 | 9/2014 | Chang et al. |
| 8,858,586 B2 | 10/2014 | Chang et al. |
| 8,858,974 B2 | 10/2014 | Eaton et al. |
| 8,864,787 B2 | 10/2014 | Muni et al. |
| 8,894,614 B2 | 11/2014 | Muni et al. |
| 8,951,225 B2 | 2/2015 | Evard et al. |
| 8,961,398 B2 | 2/2015 | Makower et al. |
| 8,961,495 B2 | 2/2015 | Chang et al. |
| 9,039,657 B2 | 5/2015 | Makower et al. |
| 9,089,258 B2 | 7/2015 | Goldfarb et al. |
| 9,101,384 B2 | 8/2015 | Makower et al. |
| 9,167,961 B2 | 10/2015 | Makower et al. |
| 9,179,823 B2 | 11/2015 | Goldfarb et al. |
| 9,216,112 B2 | 12/2015 | Clifford et al. |
| 9,265,407 B2 | 2/2016 | Goldfarb et al. |
| 9,289,576 B2 | 3/2016 | Mann et al. |
| 9,399,121 B2 | 7/2016 | Goldfarb et al. |
| 9,554,691 B2 | 1/2017 | Goldfarb et al. |
| 9,572,480 B2 | 2/2017 | Goldfarb et al. |
| 2001/0004644 A1 | 6/2001 | Levin |
| 2001/0005785 A1 | 6/2001 | Sachse |
| 2001/0034530 A1 | 10/2001 | Malackowski et al. |
| 2001/0041887 A1* | 11/2001 | Crowley ............ A61B 18/18 606/14 |
| 2002/0006961 A1 | 1/2002 | Katz et al. |
| 2002/0013548 A1 | 1/2002 | Hinchliffe |
| 2002/0055746 A1 | 5/2002 | Burke et al. |
| 2002/0077593 A1 | 6/2002 | Perkins et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0073900 A1 | 4/2003 | Senarith et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2003/0191379 A1* | 10/2003 | Benaron ............ A61B 5/0075 600/323 |
| 2003/0220551 A1 | 11/2003 | Kimball et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0137459 A1 | 6/2005 | Chin et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |

(56) References Cited

U.S. PATENT DOCUMENTS

| | | | |
|---|---|---|---|
| 2007/0020196 A1 | 1/2007 | Pipkin et al. | |
| 2007/0112358 A1 | 5/2007 | Abbott | |
| 2007/0167682 A1 | 7/2007 | Goldfarb et al. | |
| 2007/0208252 A1 | 9/2007 | Makower | |
| 2007/0250105 A1 | 10/2007 | Ressemann et al. | |
| 2007/0269385 A1 | 11/2007 | Yun et al. | |
| 2007/0293946 A1 | 12/2007 | Gonzales et al. | |
| 2008/0033519 A1 | 2/2008 | Burwell et al. | |
| 2008/0051804 A1 | 2/2008 | Cottler et al. | |
| 2008/0082045 A1* | 4/2008 | Goldfarb | A61B 1/00126 604/96.01 |
| 2008/0097516 A1 | 4/2008 | Chang et al. | |
| 2008/0103521 A1 | 5/2008 | Makower et al. | |
| 2008/0172033 A1 | 7/2008 | Keith et al. | |
| 2008/0183128 A1 | 7/2008 | Morriss et al. | |
| 2008/0188803 A1 | 8/2008 | Jang | |
| 2008/0188870 A1 | 8/2008 | Andre et al. | |
| 2008/0214959 A1 | 9/2008 | Miyata et al. | |
| 2008/0228085 A1 | 9/2008 | Jenkins et al. | |
| 2008/0275483 A1 | 11/2008 | Makower et al. | |
| 2008/0319424 A1 | 12/2008 | Muni et al. | |
| 2009/0030274 A1 | 1/2009 | Goldfarb et al. | |
| 2009/0030409 A1 | 1/2009 | Goldfarb et al. | |
| 2009/0088728 A1 | 4/2009 | Dollar et al. | |
| 2009/0163890 A1 | 6/2009 | Clifford et al. | |
| 2009/0187089 A1 | 7/2009 | Say et al. | |
| 2009/0240112 A1 | 9/2009 | Goldfarb et al. | |
| 2010/0030031 A1 | 2/2010 | Goldfarb et al. | |
| 2010/0042046 A1 | 2/2010 | Chang et al. | |
| 2010/0087811 A1 | 4/2010 | Herrin et al. | |
| 2010/0174138 A1 | 7/2010 | Chang et al. | |
| 2010/0198191 A1 | 8/2010 | Clifford et al. | |
| 2010/0198247 A1 | 8/2010 | Chang et al. | |
| 2010/0210901 A1 | 8/2010 | Makower et al. | |
| 2010/0268245 A1 | 10/2010 | Chang et al. | |
| 2010/0274188 A1 | 10/2010 | Chang et al. | |
| 2010/0298862 A1 | 11/2010 | Chang et al. | |
| 2011/0004057 A1 | 1/2011 | Goldfarb et al. | |
| 2011/0015482 A1 | 1/2011 | Carrillo, Jr. | |
| 2011/0060214 A1 | 3/2011 | Makower | |
| 2011/0112512 A1 | 5/2011 | Muni et al. | |
| 2011/0166190 A1 | 7/2011 | Anderson et al. | |
| 2012/0071710 A1 | 3/2012 | Gazdzinski | |
| 2012/0071824 A1 | 3/2012 | Chang et al. | |
| 2012/0078118 A1* | 3/2012 | Jenkins | A61B 5/065 600/478 |
| 2012/0136207 A1 | 5/2012 | Goldfarb et al. | |
| 2012/0184983 A1 | 7/2012 | Chang et al. | |
| 2012/0231529 A1 | 9/2012 | Kyle | |
| 2012/0245419 A1 | 9/2012 | Makower et al. | |
| 2012/0265094 A1 | 10/2012 | Goldfarb et al. | |
| 2013/0245608 A1 | 9/2013 | Muni et al. | |
| 2013/0261388 A1 | 10/2013 | Jenkins et al. | |
| 2016/0008017 A1 | 1/2016 | Makower et al. | |

FOREIGN PATENT DOCUMENTS

| | | |
|---|---|---|
| CN | 2151720 | 1/1994 |
| CN | 2352818 | 12/1999 |
| CN | 1561178 A | 1/2005 |
| CN | 201005758 Y | 1/2008 |
| CN | 101766469 | 7/2010 |
| DE | 3202878 | 8/1983 |
| DE | 4032096 | 4/1992 |
| DE | 4406077 | 9/1994 |
| DE | 19707740 | 9/1998 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 200430 | 11/1986 |
| EP | 257605 | 3/1988 |
| EP | 355996 | 2/1990 |
| EP | 418391 | 3/1991 |
| EP | 427852 | 5/1991 |
| EP | 515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | S 53-067935 | 6/1978 |
| JP | S61-16750 A | 1/1986 |
| JP | S 64-24098 | 1/1989 |
| JP | 10-34376 A | 2/1989 |
| JP | H01-305965 A | 12/1989 |
| JP | 3-503011 | 7/1991 |
| JP | 3-504935 | 10/1991 |
| JP | 4-221313 | 8/1992 |
| JP | H 04-224766 | 8/1992 |
| JP | 5-503650 | 6/1993 |
| JP | 5-211985 | 8/1993 |
| JP | H05-506805 A | 10/1993 |
| JP | H 6-017751 U | 3/1994 |
| JP | 6-277296 | 10/1994 |
| JP | 7-327916 | 12/1995 |
| JP | 8-317989 | 12/1996 |
| JP | H10-501159 A | 2/1998 |
| JP | H 10-94543 A | 4/1998 |
| JP | 11-507251 | 6/1999 |
| JP | 2000-501634 | 2/2000 |
| JP | 2000-126303 A | 5/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 A | 2/2004 |
| JP | 2004-357728 | 12/2004 |
| JP | 2005-323702 A | 11/2005 |
| JP | 2005-532869 | 11/2005 |
| JP | 2007-503929 A | 3/2007 |
| JP | 2008-539031 A | 11/2008 |
| JP | 2009-500051 A | 1/2009 |
| JP | 04-224766 | 2/2009 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/21320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009192 | 2/2000 |
| WO | WO 2000/009190 | 2/2000 |

(56) References Cited

FOREIGN PATENT DOCUMENTS

| WO | WO 00/023009 | 4/2000 |
|---|---|---|
| WO | WO 00/051672 | 9/2000 |
| WO | WO 00/053252 | 9/2000 |
| WO | WO 2000/067834 | 11/2000 |
| WO | WO 2001/005462 | 1/2001 |
| WO | WO 01/045572 | 6/2001 |
| WO | WO 01/054558 | 8/2001 |
| WO | WO 01/056481 | 8/2001 |
| WO | WO 01/070325 | 9/2001 |
| WO | WO 2001/068178 | 9/2001 |
| WO | WO 01/074266 | 10/2001 |
| WO | WO 01/097895 | 12/2001 |
| WO | WO 02/062269 | 8/2002 |
| WO | WO 2002/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/058045 | 7/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/035204 A2 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

European Communication dated Nov. 9, 2018 for Application No. 12175585.4, 8 pages.
U.S. Appl. No. 11/647,530.
U.S. Appl. No. 11/803,695.
U.S. Appl. No. 11/881,677.
U.S. Appl. No. 12/122,884.
U.S. Appl. No. 14/793,954.
U.S. Appl. No. 14/993,444.
Australian Office Action, Examiner's First Report dated Feb. 12, 2014 for Application No. AU 2012202103, 6 pgs.
Australian Office Action, Examination Report No. 2, dated Sep. 17, 2014 for Application No. AU 2012202103, 5 pgs.
Australian Office Action, Examination Report No. 1, dated Aug. 1, 2014 for Application No. AU 2012244072, 5 pgs.
Australian Office Action, Examination Report No. 2, dated Jul. 8, 2015 for Application No. AU 2012244072, 4 pgs.
Australian Office Action, Examiner's First Report dated Sep. 30, 2014 for Application No. AU 2009293312, 3 pages.
Australian Office Action, Examiner's First Report dated Oct. 1, 2014 for Application No. AU 2009333010, 3 pgs.
Canadian Office Action dated Jul. 10, 2015 for Application No. CA 2,617,054, 4 pgs.
Chinese Office Action, Third, for Application No. CN 200980152995.0, 3 pgs.
Chinese Office Action, Text of Decision on Rejection, for Application No. CN 200980152995.0, 4 pgs.
Chinese First Office Action and Search Report dated Jan. 21, 2015 for Application No. CN 201310672731.6, 9 pgs.
European Search Report and Written Opinion dated Sep. 15, 2015 for Application No. EP 15163549.7.
Partial European Search Report dated Oct. 16, 2012 for Application No. EP 12175585.4.
Supplemental European Search Report and Written Opinion dated Jan. 27, 2014 for Application No. EP 10842632.1.
Japanese Office Action, Notification of Reasons for Refusal dated Sep. 24, 2013 for Application No. JP 2011-527942, 4 pgs.
Japanese Office Action, Notification of Reasons for Refusal dated Nov. 12, 2013 for Application No. JP 2011-542562, 2 pgs.
Japanese Office Action, Notification of Reasons for Refusal, dated Jan. 7, 2014 for Application No. JP 2012-266049, 3 pgs.
Japanese Office Action, Notification of Reasons for Refusal, dated Sep. 2, 2014 for Application No. JP 2012-544859, 6 pgs.
Japanese Office Action, Notification of Reasons for Refusal, dated Jun. 9, 2015 for Application No. JP 2014-147174, 3 pgs.
U.S. Appl. No. 11/888,284.
U.S. Appl. No. 12/479,332.
U.S. Appl. No. 13/451,453.
U.S. Appl. No. 14/308,897.
Argon Medical, Maxxim Medical. Ad for Sniper EliteTM Hydrophilic Ni—Ti Alloy Guidewire (2001), 1 pg.
Barrett, S. 'Be Wary of Neurocranial Restructuring (NCR)' Chirobase, Jul. 2003, all pages; www.chirobase.org/06DD/ncr.html, pp. 1-4.
Bellis, M. History of the Catheter-Balloon Catheter—Thomas Fogarty; accessed 2010, www.inventors.about.com/library/inventors/blcatheter.htm?p=1, pp. 1-2.
Cussler, E.L. 'Diffusion: Mass transfer in Fluid Systems' Cambridge University Press (1996), pp. 1-3.
Domb, A. et al. 'Handbook of Biodegradable Polymers' Harwood Academic Publishers (1997), pp. 1-2.
Doyle Nasal Splints, Jan. 25, 2007, www.doylemedical.com/nasalsplints.htm, 1 pg.
Edmond, C. et al. 'ENT Surgical Stimulator' Nov. 1998 Final Report Cooperative Agreement No. DAMD17-95-2-5023; pp. 1-107.
ENT Checklist; Physical Examination Performance Checklist [date of publication unknown], pp. 1-2.
Gottmann, et al. 'Successful Treatment of Recurrent Post-Operative Frontal Sinus Stenoses by Balloon Dilatation' CIRSE (Oct. 5, 2002), pp. 1-29.
Gottman, et al., Balloon Dilatation of Recurrent Ostial Occlusion of the Front Sinus OASIS—Online Abstract Submission and Invitation System, 1996-2006, Coe Truman Technologies, Inc.
Gottman, et al. 'Balloon Dilatation of Recurrent Ostial Occlusion of the Frontal Sinus' ECR.
Gottmann, et al. 'Balloon Dilatation of Recurrent Ostial Occlusion of the Frontal Sinus' CIRSE (Mar. 2001).
Gottmann, et al. 'Balloon Dilatation of Recurrent Ostial Occlusion of the Frontal Sinus' CIRSE (Mar. 2001), pp. 1-56.
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/, pp. 1-3.
Hosemann, W.G. et al. 'Minimally Invasive Endonasal Sinus Surgery' Thieme, Stuttgart, New York (2000), pp. 1-3.
Kennedy, D.W., M.D. et al. 'Diseases of the Sinuses: Diagnosis and Management' (Copyright 2001) by B.C. Decker Inc., pp. 1-29.
K-Splint Internal Nasal Splints, Jan. 25, 2007, www.invotec.net/rhinology/ksplint.html, 1 pg.
Nasal Surgery and Accessories, Jan. 25, 2007; www.technologyforlife.com.au/ent/nasal.html.
Park, K, et al. 'Biodegradable Hydrogels for Drug Delivery' (1993) Technomic Publishing Inc. Lancaster, pp. 1-2.
Sawbones Catalog 2001, Pacific Research Laboratories, Inc., Vashon Washington 98070 USA; pp. 1-20.
Schaefer, S.D., M.D. 'Rhinology and Sinus Disease: A Problem-Oriented Approach' (Copyright 1988) by Mosby, Inc., pp. 1-38.
Schneider, Pfizer Ad for Softip [date of publication unknown], pp. 1-2.
Sinusitus, Maxillary, Acute Surgical Treatment. Http://www.emedicine.com/ent/topic340.htm. Aug. 29, 2006, pp. 1-11.

(56) References Cited

OTHER PUBLICATIONS

Strohm, et al. Die Behandlung von Stenosen der oberen Luftwege mittels rontgenologisch gesteuerter Ballondilation (Sep. 25, 1999) pp. 1-4.
SurgTrainer Product Information 2003, Surg Trainer, Ltd. Ibaraki, Japan, pp. 1-5.
SurgTrainer Product Information 'Incisive Human Nasal Model for ESS Training' Surg Trainer, Ltd. Ibaraki, Japan (2004) wwwl.acesnet.ne.jp/~juliy/st/en/partslist.hmtl; pp. 1-4.
Terumo. Medi-Tech. Boston Scientific. (1993) Ad of Glidewire, 1 pg.
Xomed-Treace. Bristol-Myers Squibb. Ad for Laser Shield II. Setting the Standards for Tommorrow. [date of publication unknown], 1 pg.
Yamauchi, Y., et al., 'A Training System for Endoscopic Sinus Surgery with Skill Evaluation' Computer Assisted Radiology and Surgery (2001) with accompanying poster presentation, pp. 1-7.
Australian Office Action, Examiners First Report dated Dec. 9, 2011 for Application No. AU 2006292818; pp. 1-2.
Australian Office Action, Examiner's First Report dated Mar. 5, 2014 for Application No. AU 2011305612.
Chinese Search Report dated Oct. 29, 2012 for Application No. CN 200980137396.1.
Chinese Search Report dated Jan. 11, 2013 for Application No. CN 200980152995.0.
Chinese Search Report dated Nov. 13, 2014 for Application No. CN 201180045789.7, 2 pages.
Chinese Examiner's Report dated Nov. 25, 2014 for Application No. CN 201180045789.7, 10 pages.
Chinese First Office Action dated Aug. 9, 2010 for Application No. 200780042221.3, 5 pages.
Chinese First Office Action dated Nov. 5, 2012 for Application No. CN 200980137396.1; pp. 1-8.
Chinese First Office Action dated Jan. 29, 2013 for Application No. CN 200980152995.1; pp. 1-7.
Chinese First Office Action dated Nov. 25, 2014 for Application No. CN 201180045789.7, 4 pages.
Chinese Second Office Action dated Jun. 15, 2011 for Application No. CN 200780042221.3.
Chinese Second Office Action dated Sep. 29, 2015 for Application No. 201180045789.7, 3 pages.
Chinese Fourth Office Action dated Aug. 24, 2012 for Application No. CN 200780042221.3, 9 pages.
European Communication dated Sep. 4, 2008 for Application No. EP 05773189; pp. 1-2.
European Communication dated Jun. 19, 2009 for Application No. EP 05773189; pp. 1-4.
European Communication dated Feb. 12, 2010 for Application No. 07836109.4, 7 pages.
European Communication dated Jun. 29, 2010 for Application No. EP 0783610934, 1 pg.
European Communication dated Jul. 20, 2010 for Application No. EP 07836110, 1 pg.
European Communication dated Aug. 1, 2012 for Application No. EP 06784759.0; pp. 1-5.
European Communication dated Aug. 24, 2012 for Application No. EP 05798331.4; pp. 1-4.
European Communication dated Nov. 9, 2012 for Application No. EP 07750248.2; pp. 1-5.
European Communication dated Apr. 19, 2012 for Application No. EP 08746715.5; pp. 1-4.
European Communication dated Jan. 7, 2013 for Application No. EP 08746715.5; pp. 1-4.
European Communication dated Apr. 11, 2013 for Application No. EP 05778834.1; pp. 1-4.
European Communication dated May 10, 2013 for Application No. EP 06751637.7; pp. 1-5.
European Communication dated Nov. 11, 2015 for Application No. 07836110.2, 4 pages.
European Communication dated Nov. 16, 2015 for Application No. 07836109.4, 4 pages.
European Examiner's Report dated Feb. 22, 2006 for Application No. EP 02716734.5.
European Examiner's Report dated Feb. 8, 2007 for Application No. EP 02716734.5.
Examiner's First Report dated Apr. 8, 2010 for Application No. AU2005274794; pp. 1-2.
European Search Report dated Mar. 16, 2010 for Application No. EP 06718986; pp. 1-4.
European Search Report dated Sep. 27, 2011 for Application No. EP 10182961; pp. 1-3.
European Search Report dated Sep. 29, 2011 for Application No. EP 10182893; pp. 1-5.
European Search Report dated Jul. 23, 2012 for Application No. EP 12162709; pp. 1-10.
European Search Report dated Jul. 24, 2012 for Application No. EP 12162712; pp. 1-9.
European Search Report dated Aug. 31, 2012 for Application No. EP 12173295; pp. 1-6.
European Search Report dated Oct. 10, 2012 for Application No. EP 12175607; pp. 1-8.
European Search Report dated Oct. 10, 2012 for Application No. EP 12175585 pp. 1-12.
European Search Report dated Nov. 22, 2012 for Application No. EP 12182993; pp. 1-7.
European Search Report dated Dec. 5, 2012 for Application No. EP 12182998; pp. 1-5.
European Search Report dated Jan. 9, 2013 for Application No. EP 12183000; pp. 1-5.
European Search Report dated Jan. 11, 2013 for Application No. EP 12183002; pp. 1-5.
European Search Report dated Aug. 13, 2013 for Application No. EP 13172140; pp. 1-7.
European Search Report dated Sep. 9, 2013 for Application No. EP 13179223; pp. 1-7.
International Preliminary Report on Patentability dated Aug. 7, 2006 for Application No. PCT/US05/25371; pp. 1-3.
International Preliminary Report on Patentability dated Sep. 25, 2007 for Application No. PCT/US06/02004; pp. 1-6.
International Preliminary Report on Patentability dated Feb. 15, 2008 for Application No. PCT/US05/13617; pp. 1-5.
International Preliminary Report on Patentability dated Nov. 18, 2008 for Application No. PCT/US07/11449; pp. 1-4.
International Preliminary Report on Patentability dated Apr. 7, 2009 for Application No. PCT/US07/021170; pp. 1-16.
International Preliminary Report on Patentability dated May 5, 2009 for Application No. PCT/US06/36960; pp. 1-4.
International Preliminary Report on Patentability dated Oct. 13, 2009 for Application No. PCT/US08/059786; pp. 1-8.
International Preliminary Report on Patentability dated Oct. 27, 2009 for Application No. PCT/US08/061343; pp. 1-14.
International Preliminary Report on Patentability dated Jun. 29, 2011 for Application No. PCT/US2009/069143; pp. 1-6.
International Preliminary Report on Patentability dated Mar. 26, 2013 for Application No. PCT/US2011/052321.
International Search Report dated Jun. 3, 2002 for Application No. PCT/EP2002/01228; pp. 1-3.
International Search Report dated May 8, 2007 for Application No. PCT/US2006/16026; pp. 1-4.
International Search Report dated Aug. 17, 2007 for Application No. PCT/US2005/13617; pp. 1-8.
International Search Report dated Aug. 29, 2007 for Application No. PCT/US2006/02004; pp. 1-4.
International Search Report dated Sep. 25, 2007 for Application No. PCT/US2006/37167; pp. 1-3.
International Search Report dated Oct. 19, 2007 for Application No. PCT/US2007/03394; pp. 1-3.
International Search Report dated May 29, 2008 for Application No. PCT/US2007/21170; pp. 1-5.
International Search Report dated May 29, 2008 for Application No. PCT/US2007/21922; pp. 1-3.

(56) References Cited

OTHER PUBLICATIONS

International Search Report dated Jul. 1, 2008 for Application No. PCT/US2006/22745; pp. 1-4.
International Search Report dated Jul. 3, 2008 for Application No. PCT/US2006/29695; pp. 1-3.
International Search Report dated Jul. 7, 2008 for Application No. PCT/US2007/16213; pp. 1-3.
International Search Report dated Jul. 8, 2008 for Application No. PCT/US2007/11474; pp. 1-2.
International Search Report dated Jul. 17, 2008 for Application No. PCT/US2006/36960; pp. 1-2.
International Search Report dated Aug. 25, 2008 for Application No. PCT/US2008/000911; pp. 1-5.
International Search Report dated Sep. 10, 2008 for Application No. PCT/US2007/016212; pp. 1-2.
International Search Report dated Oct. 15, 2008 for Application No. PCT/US2008/061048; pp. 1-4.
International Search Report dated Nov. 30, 2009 for Application No. PCT/US2009/057203; pp. 1-4.
International Search Report dated Dec. 10, 2009 for Application No. PCT/US2009/052236; pp. 1-6.
International Search Report dated Dec. 16, 2009 for Application No. PCT/US2009/050800; pp. 1-6.
International Search Report dated Mar. 31, 2010 for Application No. PCT/US2009/069143; pp. 1-4.
International Search Report dated Jul. 8, 2010 for Application No. PCT/US2010/027837; pp. 1-4.
International Search Report dated Mar. 25, 2011 for Application No. PCT/US2010/062161; pp. 1-5.
International Search Report dated Mar. 28, 2011 for Application No. PCT/US2010/061850; pp. 1-4.
International Search Report dated Mar. 31, 2011 for Application No. PCT/US2010/060898; pp. 1-2.
International Search Report dated Mar. 31, 2011 for Application No. PCT/US2009/069143; pp. 1-4.
International Search Report dated Aug. 9, 2011 for Application No. PCT/US2011/038751; pp. 1-6.
International Search Report dated May 18, 2012 for Application No. PCT/US2011/052321; pp. 1-5.
International Search Report and Written Opinion dated Apr. 10, 2006 for Application No. PCT/US05/25371; pp. 1-6.
International Search Report and Written Opinion dated Jul. 21, 2008 for Application No. PCT/US05/033090; pp. 1-5.
International Search Report and Written Opinion dated Sep. 12, 2008 for Application No. PCT/US07/16214; pp. 1-8.
International Search Report and Written Opinion dated Sep. 17, 2008 for Application No. PCT/US08/059786; pp. 1-11.
International Search Report and Written Opinion dated Sep. 17, 2008 for Application No. PCT/US08/061343; pp. 1-15.
International Search Report and Written Opinion dated Oct. 1, 2008 for Application No. PCT/US07/011449; pp. 1-5.
International Search Report and Written Opinion dated Oct. 6, 2010 for Application No. PCT/US2010/040548; pp. 1-18.
Japanese Office Action, Notification of Reasons for Refusal, dated Apr. 26, 2011 for Application No. JP 2007-532485.
Japanese Office Action, Notification of Reasons for Refusal, dated Aug. 16, 2011 for Application No. JP 2008-516013.
Japanese Office Action, Notification of Reasons for Refusal, dated Oct. 18, 2011 for Application No. JP 2007-509632.
Japanese Office Action, Notification of Reasons for Refusal, dated Nov. 8, 2011 for Application No. JP 2008-524250.
Japanese Office Action, Notification of Reasons for Refusal, dated Jan. 24, 2012 for Application No. JP 2007-532485.
Japanese Office Action, Notification of Reasons for Refusal, dated Jun. 25, 2013 for Application No. JP 2012-131840.
Japanese Office Action, Notification of Reasons for Refusal, dated Jul. 14, 2015 for Application No. 2013-530227, 6 pages.
Mexican Office Action dated May 11, 2015 for Application No. MX/a/2013/003283.
Mexican Office Action dated Oct. 5, 2015 for Application No. MX/a/2013/003283.
Partial European Search Report dated Sep. 20, 2007 for Application No. EP 07252018.
Partial European Search Report dated Mar. 25, 2008 for Application No. EP 07252018.
Partial International Search Report dated Feb. 7, 2012 for Application No. PCT/US2011/052321; pp. 1-2.
Russian Office Action dated Sep. 28, 2012 for Application No. RU 2011130530.
Russian Office Action dated Mar. 19, 2013 for Application No. RU 2011130530.
Supplemental Partial European Search Report dated Jun. 2, 2008 for Application No. EP 05773189; pp. 1-8.
Supplemental Partial European Search Report dated Jul. 1, 2009 for Application No. EP 06815285; pp. 1-4.
Supplemental Partial European Search Report dated Nov. 19, 2010 for Application No. EP 06751637; pp. 1-7.
Supplemental European Search Report dated Jan. 29, 2010 for Application No. EP 07836108; pp. 1-2.
Supplemental European Search Report dated Feb. 2, 2010 for Application No. EP 07836109; pp. 1-2.
Supplemental European Search Report dated Feb. 17, 2010 for Application No. EP 07836110; pp. 1-11.
Supplemental European Search Report dated Mar. 1, 2010 for Application No. EP 05778834; pp. 1-5.
Supplemental European Search Report dated Mar. 16, 2010 for Application No. EP 06718986; pp. 1-2.
Supplemental European Search Report dated Jun. 22, 2010 for Application No. EP 06784759; pp. 1-10.
Supplemental European Search Report dated Sep. 23, 2010 for Application No. EP 08746715; pp. 1-2.
Supplemental European Search Report dated Jan. 28, 2011 for Application No. EP 07777004; pp. 1-3.
Supplemental European Search Report dated Mar. 31, 2011 for Application No. EP 05798331; pp. 1-2.
Supplemental European Search Report dated Aug. 30, 2011 for Application No. EP 06800540; pp. 1-4.
Supplemental European Search Report dated Sep. 29, 2011 for Application No. EP 07750248; pp. 1-2.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 11/648,158, filed Dec. 29, 2006.
U.S. Appl. No. 11/804,308, filed May 16, 2007.
U.S. Appl. No. 11/804,309, filed May 16, 2007.
U.S. Appl. No. 13/840,430, filed Mar. 15, 2013.
International Preliminary Report on Patentability dated Dec. 4, 2012 for Application No. PCT/US2011/038751, 9 pgs.
Japanese Office Action, Notification of Reasons for Refusal, dated Mar. 29, 2016 for Application No. JP 2012-266049, 6 pgs.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.

(56) References Cited

OTHER PUBLICATIONS

USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
Chinese Office Action, Third, dated Mar. 20, 2012 for Application No. CN 200780042221.3, 5 pgs.
European Search Report and Written Opinion dated Sep. 11, 2009 for Application No. EP 06815174.
International Search Report dated Mar. 31, 2010 for Application No. PCT/US2009/069143.
Aust, R., et al. 'The Functional Size of the Human Maxillary Ostium in Vivo' Acta. Otolaryn. (9178) vol. 78 pp. 432-435.
Baim, D.S., MD 'Grossman's Cardiac Catheterization, Angiography, and Intervention' (2000) Lippincott Williams & Wilkins pp. 76, 84 & 214.
Bartal, N. 'An Improved stent for Use in the Surgical Management of Congential Posterior Choanal Atresia' Laryngol. Otol (1988) vol. 102 pp. 146-147.
Becker, A.E. 'Restenosis After Angioplasty' The Lancet (1988) vol. 331, No. 8584 p. 532.
Benninger et al.; Adult Chronic Rhinosinusitis: Defintions, Diagnosis, Epidemiology, and Pathophysilogy Arch Otolarygol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: The University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers—General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Croix et al., "Genes expressed in human endothelium," Science Aug. 18, 2000; 289(5482):1197-1202.
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Draf, W. 'Endonasal Micro-Endoscopic Frontal Sinus Surgery: the Fulda Concept' Op Tech Otolaryngol Head Neck Surg. vol. 2 (1991) pp. 234-240.
Dymax, "Single-Pole and Multi-Pole Lightguides for UVNisible Spot Light Curing Systems"; retrieved from the Internet: http://www.dymax.com/products/curing_equipment/lightguides/lightguides_single_and_multi.php, 2004, 2 pages total.
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.

(56) References Cited

OTHER PUBLICATIONS

Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence ot Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE.(Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7. No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, M.E. et al. 'Normal Wound Healing of the Paranasal Sinuses—Clinical and Experimental Investigations' Eur Arch Otorhinolaryngol. vol. 248, (1991) pp. 390-394.
Hosemann, W. et al. 'Behandlung nach Nasennebenhohleneingriffen, part 2: Theapeutische Maßnahem' HNO akutell 7 (1999) pp. 291-302.
Hospital Corpsman Sickcall Screener's Handbook. Naval Hospital Great Lakes (Apr. 1999) www.brooksidepress.org/Products/Operationa. Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
Kaiser, H. et al 'Cortizontherapie, Corticoide in Klinik und Praxis' Thieme, Stuggart (1992) pp. 390-401.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.

Kingdom, T.T. et al. 'Image-Guided Surgery of the Sinuses: Current Technology and Applications' Otolaryngol. Clin. North Am. vol. 37. No. 2 (Apr. 2004) pp. 381-400.
Klossek, J.M. et al. 'Local Safety of Intranasal Trimcinolone Acentonide: Clinical and Histological Aspects of Nasal Mucosa In the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Labiberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com-MicroFrance Catalog Browser. www.xomcat.com/xomfrance/index.php?zone=both&cat=18&sub=58&prodline=1272 (Dec. 31, 2003) pp. 1-2.
Medtronic; "Vaughan Suction Sinus Instruments," [Online Catalog] xomed.com-MicroFrance Catalog Browser Dec. 31, 2003; retrieved from the Internet: http://www.xonncat.com/xomfrance/index.php?zone=both&cat=18&sub=58&prodline=1272, 2 pages total.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Piccirillo, J.F. et al. 'Physchometric and Clinimetric Validity of the 20-Item Sino-Nasal Outcome test (SNOT-20)' Copyiight 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.

(56) References Cited

OTHER PUBLICATIONS

Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' TEXAS State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Saxon, R.R. et al., 'Technical Aspects of Accessing the Portal Vein During the TIPS Procedure' J. Vasc. Interv. Radiol. (1997) vol. 8, No. 5 pp. 733-744.
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al 'Le Traitenment Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Yamauchi, Y. et al., 'Development of a Silicone Model for Endoscopic Sinus Surgery' Proc International Journal of Computer Assisted Radiology and Surgery vol. 99 (1999) p. 1039.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
U.S. Appl. No. 10/259,300, filed Sep. 30, 2002.
U.S. Appl. No. 10/259,630, filed Sep. 30, 2002.
U.S. Appl. No. 10/470,881, filed Feb. 4, 2004.
U.S. Appl. No. 10/829,917, filed Apr. 21, 2004.
U.S. Appl. No. 10/912,578, filed Aug. 4, 2004.
U.S. Appl. No. 10/944,270, filed Sep. 17, 2004.
U.S. Appl. No. 11/037,548, filed Jan. 18, 2005.
U.S. Appl. No. 11/116,118, filed Apr. 26, 2005.
U.S. Appl. No. 11/150,847, filed Jun. 10, 2005.
U.S. Appl. No. 11/193,020, filed Jul. 29, 2005.
U.S. Appl. No. 11/234,395, filed Sep. 23, 2005.
U.S. Appl. No. 11/347,147, filed Feb. 2, 2006.
U.S. Appl. No. 11/355,512, filed Feb. 16, 2006.
U.S. Appl. No. 11/436,892, filed May 17, 2006.
U.S. Appl. No. 11/436,897, filed May 17, 2006.
U.S. Appl. No. 11/438,090, filed May 18, 2006.
U.S. Appl. No. 11/522,497, filed Sep. 15, 2006.
U.S. Appl. No. 11/527,773, filed Sep. 25, 2006.
U.S. Appl. No. 11/544,009, filed Oct. 4, 2006.
U.S. Appl. No. 11/647,530, filed Dec. 27, 2006.
U.S. Appl. No. 11/648,159, filed Dec. 29, 2006.
U.S. Appl. No. 11/655,794, filed Jan. 18, 2007.
U.S. Appl. No. 11/725,151, filed Mar. 15, 2007.
U.S. Appl. No. 11/789,704, filed Apr. 24, 2007.
U.S. Appl. No. 11/789,705, filed Apr. 24, 2007.
U.S. Appl. No. 11/803,695, filed May 14, 2007.
U.S. Appl. No. 11/925,540, filed Oct. 26, 2007.
U.S. Appl. No. 11/926,326, filed Oct. 29, 2007.
U.S. Appl. No. 11/926,565, filed Oct. 29, 2007.
U.S. Appl. No. 11/928,097, filed Oct. 30, 2007.
U.S. Appl. No. 12/011,100, filed Jan. 23, 2008.
U.S. Appl. No. 12/100,361, filed Apr. 9, 2008.
U.S. Appl. No. 12/117,582, filed May 8, 2008.
U.S. Appl. No. 12/117,672, filed May 8, 2008.
U.S. Appl. No. 12/117,961, filed May 9, 2008.
U.S. Appl. No. 12/118,931, filed May 12, 2008.
U.S. Appl. No. 12/120,902, filed May 15, 2008.
U.S. Appl. No. 12/122,884, filed May 19, 2008.
U.S. Appl. No. 12/340,226, filed Dec. 19, 2008.
U.S. Appl. No. 12/341,602, filed Dec. 22, 2008.
U.S. Appl. No. 12/502,101, filed Jul. 13, 2009.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.

\* cited by examiner

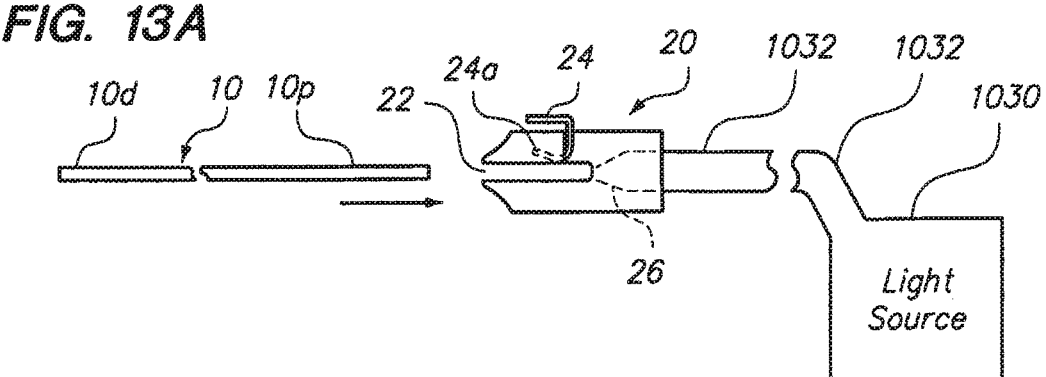
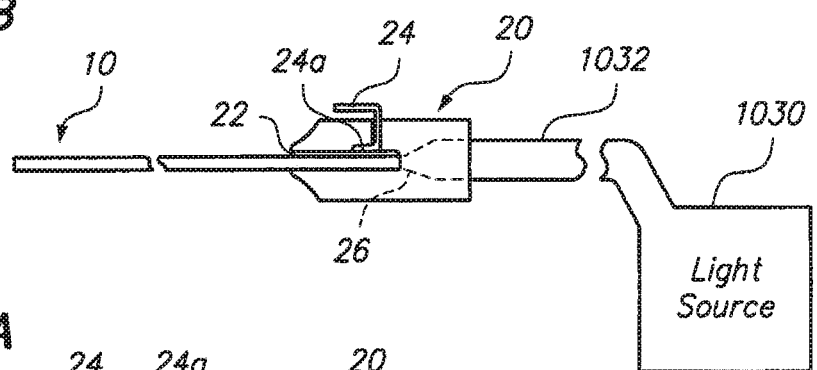
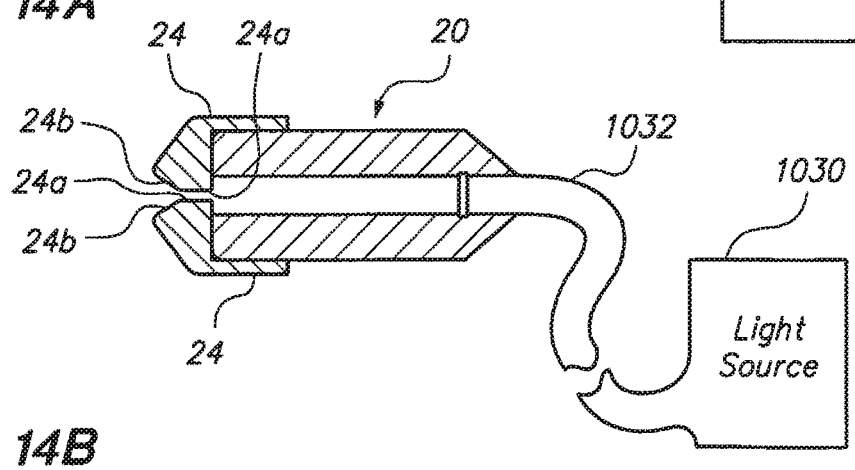
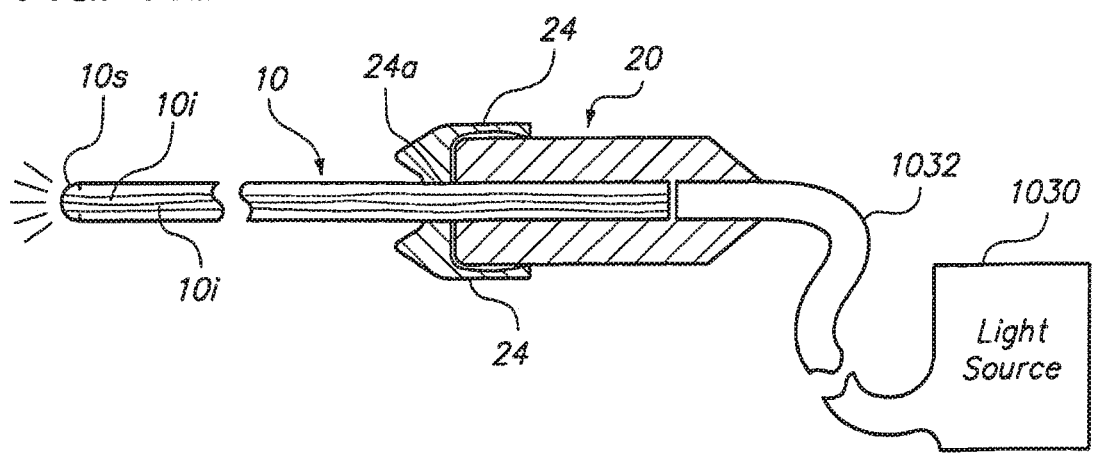

METHODS AND DEVICES FOR FACILITATING VISUALIZATION IN A SURGICAL ENVIRONMENT

CROSS REFERENCE TO RELATED APPLICATION DATA

The present application is a Continuation of prior U.S. patent application Ser. No. 12/479,332, entitled "Methods and Devices for Facilitating Visualization in a Surgical Environment," filed Jun. 5, 2009, and issued as U.S. Pat. No. 9,603,506 on Mar. 28, 2017, which is a Continuation of U.S. patent application Ser. No. 11/522,497 filed Sep. 15, 2006, now U.S. Pat. No. 7,559,925, issued Jul. 14, 2009, the full disclosure of which is incorporated by reference in its entirety.

FIELD OF THE INVENTION

The present invention relates generally to medical devices, systems and methods and more particularly to methods and devices for performing minimally invasive procedures that reduce the need to provide fluoroscopic or other radiographic visualization.

BACKGROUND OF THE INVENTION

The skull contains a series of cavities known as paranasal sinuses that are connected by passageways. The paranasal sinuses include frontal sinuses, ethmoid sinuses, sphenoid sinuses and maxillary sinuses. The paranasal sinuses are lined with mucous-producing mucosal tissue and ultimately open into the nasal cavity. Normally, mucous produced by the mucosal tissue slowly drains out of each sinus through an opening known as an ostium. If the mucosal tissue of one of these passageways becomes inflamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months or so) results in 18 million to 22 million physician office visits per year in the United States. Patients who suffer from sinusitis typically experience at least some of the following symptoms: headaches or facial pain; nasal congestion or post-nasal drainage; difficulty breathing through one or both nostrils; bad breath; and/or pain in the upper teeth.

One of the ways to treat sinusitis is by restoring the lost mucous flow. The initial therapy is typically drug therapy using anti-inflammatory agents to reduce the inflammation and antibiotics to treat the infection. A large number of patients do not respond to drug therapy. Currently, the gold standard for patients with chronic sinusitis that do not respond to drug therapy is a corrective surgery called Functional Endoscopic Sinus Surgery (FESS).

During FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures are typically performed with the patient under general anesthesia.

Although FESS continues to be the gold standard therapy for surgical treatment of severe sinus disease, FESS does have several shortcomings. For example, FESS can cause significant post-operative pain. Also, some FESS procedures are associated with significant postoperative bleeding and, as a result, nasal packing is frequently placed in the patient's nose for some period of time following the surgery. Such nasal packing can be uncomfortable and can interfere with normal breathing, eating, drinking etc. Also, some patients remain symptomatic even after multiple FESS surgeries. Additionally, some FESS procedures are associated with risks of iatrogenic orbital, intracranial and sinonasal injury. Many otolaryngologists consider FESS an option only for patients who suffer from severe sinus disease (e.g., those showing significant abnormalities under CT scan). Thus, patients with less severe disease may not be considered candidates for FESS. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those anatomical structures are part of the pathology.

New devices, systems and techniques are being developed for the treatment of sinusitis and other disorders of the ear, nose, throat and paranasal sinuses. For example, various catheters, guidewires and other devices useable to perform minimally invasive, minimally traumatic ear, nose and throat surgery have been described in U.S. patent application Ser. No. 10/829,917 entitled "Devices, Systems and Methods for Diagnosing and Treating Sinusitis and Other Disorders of the Ears, Nose and/or Throat," now U.S. Pat. No. 7,654,997, issued Feb. 2, 2010; Ser. No. 10/912,578 entitled "Implantable Device and Methods for Delivering Drugs and Other Substances to Treat Sinusitis and Other Disorders," now U.S. Pat. No. 7,361,168, issued Apr. 22, 2008; Ser. No. 10/944,270 entitled "Apparatus and Methods for Dilating and Modifying Ostia of Paranasal Sinuses and Other Intranasal or Paranasal Structures" published as U.S. Pat. Pub. No. 2006/0004323 on Jan. 5, 2006; Ser. No. 11/037,548 entitled "Devices, Systems and Methods For Treating Disorders of the Ear, Nose and Throat," now U.S. Pat. No. 7,462,175, issued Dec. 9, 2008; and Ser. No. 11/116,118 entitled "Methods and Devices For Performing Procedures Within the Ear, Nose, Throat and Paranasal Sinuses," now U.S. Pat. No. 7,720,521, issued May 18, 2010. Each of these applications is hereby incorporated herein, in its entirety, by reference thereto. Many of these new devices, systems and techniques are useable in conjunction with endoscopic, radiographic and/or electronic assistance to facilitate precise positioning and movement of catheters, guidewires and other devices within the ear, nose, throat and paranasal sinuses and to avoid undesirable trauma or damage to critical anatomical structures such as the eyes, facial nerves and brain.

For example, in one new procedure (referred to in this patent application as a "Flexible Transnasal Sinus Intervention" or FTSI), a dilatation catheter (e.g., a balloon catheter or other type of dilator) is advanced through the nose to a position within the ostium of a paranasal sinus or other location, without requiring removal or surgical alteration of other intranasal anatomical structures. The dilatation catheter is then used to dilate the ostium or other anatomical structures to facilitate natural drainage from the sinus cavity. In some cases, a tubular guide may be initially inserted through the nose and advanced to a position near the sinus ostium and a guidewire may then be advanced through the tubular guide and into the affected paranasal sinus. The dilatation catheter may then be advanced over the guidewire and through the tubular guide to a position where its dilator (e.g., balloon) is positioned within the sinus ostium. The dilator (e.g., balloon) is then expanded causing the ostium to dilate. In some cases, such dilatation of the ostium may fracture, move or remodel bony structures that surround or are adjacent to the ostium. Optionally, in some procedures, irrigation solution and/or therapeutic agents may be infused through a lumen of the dilatation catheter and/or other working devices (e.g., guidewires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may be advanced through the tubular guide and/or over the guidewire to deliver other therapy to the sinus or adjacent tissues during the same procedure in which the FTSI is carried out. It is to be understood that, in FTSI procedures, structures and passageways other than sinus ostia may be dilated using the tools described above, tissue may be resected or ablated, bone may be restructured, drugs or drug delivery systems may be deployed, etc., as described in the documents incorporated herein by reference. Thus, for the purposes of this application the term FTSI will be generally used to refer broadly to all of those procedures, not just dilation of sinus ostia.

In FTSI procedures that include positioning of a guidewire into a paranasal sinus, the placement of the guidewire is typically confirmed by visualizing the procedure under fluoroscopy or other x-ray visualization technique, for example. Appropriate positioning of the tubular guide at the position near the sinus ostium may also be confirmed via fluoroscopy. In order to reduce the radiation exposure to the patient undergoing the procedure, and particularly to the surgeon and other personnel that carry out many of these types of procedures, there is a need for methods and devices that eliminate or reduce the need to use fluoroscopic visualization during such procedures.

SUMMARY OF THE INVENTION

A method for visually confirming the positioning of a distal end portion of a device placed within a patient is provided to include: inserting a distal end portion of an illuminating device internally into a patient, emitting light from the distal end portion of the illuminating device; observing transillumination resulting from the light emitted from the distal end portion of the illuminating device that occurs on an external surface of the patient; and correlating the location of the observed transillumination on the external surface of the patient with an internal location of the patient that underlies the location of observed transillumination, to confirm positioning of the distal end portion of the illuminating device.

In at least one embodiment, the observation is performed by direct line of sight human observation, without the need for fluoroscopy.

In at least one embodiment, the observation is performed by direct line of sight human observation, without the need for any visualization equipment.

In at least one embodiment, the illuminating device comprises a guidewire.

In at least one embodiment, the illuminating device comprises an ostium seeker device.

In at least one embodiment, the illuminating device comprises a sinus suction instrument.

In at least one embodiment, the illuminating device comprises an integrated wire dilatation catheter, wherein an integrated illuminating guidewire extends distally of a distal end of a dilatation catheter.

In at least one embodiment, the distal end portion of the illuminating guidewire is inserted into a sinus passageway of the patient.

In at least one embodiment, the distal end portion of the illuminating guidewire is inserted through an ostium opening to a sinus of the patient, and the distal end portion is advanced into the sinus.

In at least one embodiment, the distal end portion of the illuminating guidewire is initially inserted through a nostril of the patient and then advanced into a sinus.

In at least one embodiment, a scope is inserted through the nostril of the patient, wherein the guidewire is inserted adjacent the scope, and visualization of the advancement of the distal end portion of the guidewire is performed via the scope as the distal end portion is advanced toward an ostium of the sinus.

In at least one embodiment, transillumination is observed when a light emitting portion of the distal end portion is located in the sinus of the patient.

If observation of transillumination and correlation reveals that the distal end portion of the illumination device has been misrouted to a location other than a target location, distal end portion of the device can be retracted and re-routed to the target location, which can be confirmed by observing transillumination and correlating.

In observing transillumination, the motion of the transillumination spot resulting from the light emitted from the distal end portion of the illuminating device can be observed and tracked or followed visually, as the distal end portion is moved relative to the patient, and this can be one way of confirming that the transillumination spot in motion correlates to a position of the distal end portion. This technique can be particularly useful when there are additional sources of transillumination, such as a light from a scope, for example.

Further, transillumination resulting from the light emitted from the distal end portion of the device can be distinguished from transillumination resulting from light emitted from a scope by identifying a transillumination spot that is at least one of brighter, smaller or more well-defined than other transillumination effects observed. Alternatively, the transillumination resulting from the light emitted from the distal end portion of the device can be distinguished from transillumination resulting from light emitted from a scope by turning off or down the light source to the scope.

In at least one embodiment, a sinus guide is inserted within the patient prior to inserting the device, and the distal end portion of the illuminating device is inserted through the sinus guide.

In at least one embodiment, the illuminating device is preloaded in the guide, and the guide and preloaded illuminating device are inserted together into the patient. Advancement of the illuminating device relative to the guide can then be performed to extend a distal end portion of the illuminating device distally of a distal end of the guide.

A scope may be inserted within the patient, wherein the sinus guide is inserted adjacent the scope, and advancement of the sinus guide can be visualized via the scope.

In at least one embodiment, visualization of the advancement of the sinus guide is through use of the scope, up to a limit of adequate illumination by the scope. After that, the light emitted by the distal end portion of the illuminating device, having been advanced distally of a distal end of the sinus guide, extends the limit of adequate illumination of the scope, thereby extending a length of the adequate illumination of the scope.

In at least one embodiment, the sinus guide can be further distally advanced under visualization by the scope as facilitated by the extended length of the adequate illumination.

In at least one embodiment, visualization of the advancement of the illuminating device distally of the sinus guide can be performed via the scope, as facilitated by the light emitted from the distal end portion of the device.

In at least one embodiment, the scope is inserted into a nostril of the patient, and the sinus guide is inserted adjacent the scope.

In at least one embodiment, the scope and sinus guide are advanced into a sinus passageway of the patient.

In at least one embodiment, the sinus guide is further advanced toward an ostium of a sinus, and the advancement of the sinus guide is visually observed via the scope.

In at least one embodiment, the scope is inserted into a nostril of the patient, and the sinus guide is inserted adjacent the scope. The advancement of the sinus guide into a sinus passageway is visualized via the scope until a distal end of the sinus guide has reached a distal limit of illumination emitted by the scope.

In at least one embodiment, further advancement of the sinus guide toward an ostium of a sinus is visualized via the scope as facilitated by the extended length of adequate illumination provided by the illumination device.

In at least one embodiment, the scope is inserted into a nostril of the patient, and the sinus guide is inserted adjacent the scope. The advancement of the sinus guide to place a distal end of the sinus guide adjacent an approach to an ostium of a sinus is visualized via the scope.

In at least one embodiment, the distal end portion of the illuminating device is advanced further distally of a distal end of the sinus guide and distal of the limit of illumination of the scope to emit illumination, thereby extending a length of a space that is visualizable by the scope.

In at least one embodiment, the distal end portion of the device is further advanced into and through the ostium, and visualization of the advancement of the distal end portion into the ostium is performed via the scope.

In at least one embodiment the device comprises an illuminating guidewire, a working device is advanced over the guidewire to position a working end of the working device at a target location, and a surgical procedure is performed with the working device at the target location. The working device is removed from the patient after performing the surgical procedure. Optionally, an implant can be left at the target location.

A method of performing a minimally invasive surgical procedure is provided, including the steps of: inserting a distal end portion of an illuminating guidewire internally into a patient; emitting light from the distal end portion of the illuminating guidewire, wherein a proximal end portion is connected to a power source to enable the distal end portion to emit light; observing transillumination resulting from the light emitted from the distal end portion of the illuminating guidewire that occurs on an external surface of the patient; correlating the location of the observed transillumination on the external surface of the patient with an internal location of the patient that underlies the location of observed transillumination, to confirm positioning of the distal end portion of the illuminating guidewire; disconnecting the proximal end portion of the illuminating guidewire from the power source; advancing a working device over the guidewire so that a proximal end of the guidewire extends proximally from the working device; reconnecting the proximal end portion of the illuminating guidewire to the power source so that the distal end portion of the guidewire again emits light; positioning a working end of the working device at a target location; and performing a surgical procedure with the working device at the target location.

After performing the surgical procedure, the proximal end portion of the illuminating guidewire is disconnected from the power source; and the working device is removed from the patient and from the guidewire. Optionally, an implant can be left at the target location.

In at least one embodiment, a second working device is advanced over the guidewire after removing the first working device therefrom, so that a proximal end of the guidewire extends proximally from the second working device. Then the proximal end portion of the illuminating guidewire is reconnected to the power source so that the distal end portion of the guidewire again emits light.

In at least one embodiment, the illuminating guidewire includes at least one illumination fiber extending from a proximal end of the guidewire to the distal end portion, and the power source is a light source.

In at least one embodiment, the illuminating guidewire includes at least one laser fiber extending from a proximal end of the guidewire to the distal end portion, and the power source is a laser light source.

In at least one embodiment, the illuminating guidewire includes a light emitting diode at the distal end portion and electrical wires extending through the guidewire, electrically connecting the light emitting diode to the power source, and wherein the power source is an electrical power source.

A method for diagnosing and/or treating sinusitis or another disorder affecting a nose, a sinus or other anatomical structure of the ear, nose or throat in a human or animal patient is provided, including the steps of: advancing an introducing device through the nose and to a position where the distal end of the introducing device is near an opening of a sinus; advancing a distal end portion of an illuminating device that emits light from the distal end portion thereof through the introducing device while a proximal end of the illuminating device is connected to a power source; and monitoring a position of the distal end portion of the illuminating device distally of the distal end of the introducing device, by observing transillumination on an external surface of the patient that results from the light emitted by the distal end portion. The light emitted can be a desired wavelength in the visible spectrum and/or infrared spectrum.

In at least one embodiment, the distal end portion of the illuminating device is advanced through the opening of the sinus; and placement of the distal end portion of the illuminating device in the sinus is confirmed by observing the transillumination resulting from the light emitted from the distal end portion of the illuminating device that occurs on the external surface of the patient, and correlating the location of the observed transillumination on the external surface of the patient with an internal location of the patient that underlies the location of observed transillumination.

In at least one embodiment, the external surface on which the transillumination is observed is on the face of the patient.

In at least one embodiment, the external surface on which the transillumination is observed is on the palate of the patient.

In at least one embodiment the illuminating device comprises an illuminating guidewire, and a working device is provided that is positionable in an operative location and useable to perform a diagnostic or therapeutic procedure there. The proximal end of the illuminating guidewire is disconnected from the power source, while maintaining the distal end portion of the illuminating guidewire in its current position, and the working device is advanced over the guidewire so that a proximal end of the guidewire extends proximally from the working device. The proximal end of the illuminating guidewire is then reconnected to the power source so that the distal end portion of the guidewire again emits light. The working device is further advanced to position a working end of the working device at the operative location, and a diagnostic or therapeutic procedure is performed with the working device at the operative location.

In at least one embodiment, the operative location is the opening to the sinus.

An illuminating guidewire device is provided, including: a flexible distal end portion; a relatively less flexible proximal end portion; at least one light emitting element in the distal end portion; and at least one structure extending from a proximal end of the device through the proximal end portion and at least part of the distal end portion to connect the at least one light emitting element with a power source located proximally of the device.

In at least one embodiment, the at least one light emitting element comprises a distal end of at least one illumination fiber, and the at least one structure comprises the at least one illumination fiber running proximally of the distal end of the fiber to the proximal end of the device.

In at least one embodiment, the power source is a light source.

In at least one embodiment, the at least one light emitting element of the illuminating guidewire comprises a distal end of at least one laser fiber, and the at least one structure comprises the at least one laser fiber running proximally from the distal end of the fiber to the proximal end of the device.

In at least one embodiment, the power source is a laser light source.

In at least one embodiment, the at least one light emitting element comprises a light emitting diode, and the at least one structure comprises at least one electrical wire electrically connected to the light emitting diode and extending proximally of the light emitting diode to the proximal end of the device.

In at least one embodiment, the power source is an electrical power source.

In at least one embodiment, the distal end portion of the guidewire has an outside diameter configured and dimensioned to pass through an ostium of a sinus.

In at least one embodiment, the distal end portion of the guidewire has an outside diameter less than about 0.038 inches.

In at least one embodiment, the distal end portion of the guidewire has an outside diameter of about 0.035"±0.005".

In at least one embodiment, the illuminating guidewire has a maximum outside diameter of less than about 0.038 inches.

In at least one embodiment, the illuminating guidewire has a maximum outside diameter of less than about 0.035 inches.

In at least one embodiment, the illuminating guidewire has a maximum outside diameter of about 0.035"±0.005".

In at least one embodiment, the distal end portion of the device comprises a flexible coil. In at least one embodiment, the distal end portion further comprises a core support extending internally of the coil. In at least one embodiment, the core support is fixed to the coil.

In at least one embodiment, a core support extending within the distal and proximal end portions of the device. In at least one embodiment, the core support extends within substantially the full length of the distal and proximal end portions.

In at least one embodiment, the distal end portion of the device includes a bend, such that a proximal part of the distal end portion is substantially aligned with a longitudinal axis of the device, and a distal part of the distal end portion is angled with respect to the longitudinal axis.

In at least one embodiment, the distal end of at least one illumination fiber is configured to emit light from a distal tip of the distal end portion of the device. The distal tip can be designed to either focus or distribute the light to achieve maximum transillumination. The distal tip can include a lens, prism or diffracting element.

In at least one embodiment, the distal end of at least one illumination fiber is positioned proximally of a distal tip of the distal end portion of the device.

In at least one embodiment, a flexible distal portion of the distal end portion extends distally of the distal end of the at least one illumination fiber.

In at least one embodiment, the distal end of at least one laser fiber is configured to emit light from a distal tip of the distal end portion of the device.

In at least one embodiment, the distal end of at least one laser fiber is positioned proximally of a distal tip of the distal end portion of the device.

In at least one embodiment, a flexible distal portion of the distal end portion extends distally of the distal end of at least one illumination fiber.

In at least one embodiment, a light emitting diode is mounted at a distal tip of the distal end portion of the device.

In at least one embodiment, a light emitting diode is positioned proximally of a distal tip of the distal end portion of the device. In at least one embodiment, a flexible distal portion of the distal end portion extends distally of the light emitting diode.

In at least one embodiment, an electrical power source is removably, electrically connected to at least one structure to provide electrical power to at least one light emitting element.

In at least one embodiment, at least one light conducting tube delivers light from a proximal end portion of the device to a distal and of the tube, where it is emitted.

In at least one embodiment, each light conducting tube is sealed in a proximal end of the device.

In at least one embodiment, each light emitting element is sealed at a distal tip of the device.

In at least one embodiment, a quick release connector is mounted over at least part of the proximal end portion of the guidewire. The quick release connector is adapted to be connected to a power source and to quickly connect to and release from the proximal end portion of the guidewire.

In at least one embodiment, the quick release connector is optically coupled with a light source.

In at least one embodiment, the proximal end portion of the quick release connector is adapted to connect with a light source.

In at least one embodiment, the proximal end portion of the quick release connector comprises an ACMI light post.

In at least one embodiment, the connector is rotatable with respect to a light channel extending from a light source, when the connector is connected to the light channel. In at least one embodiment, the light cable comprises a fluid filled light cable.

In at least one embodiment, a distal end portion of the connector comprises an opening configured to slidably receive the proximal end portion of the guidewire device; and a quick release locking mechanism is configured to fix the proximal end portion received in the connector.

In at least one embodiment, the quick release locking mechanism is movable between an unlocked configuration in which the proximal end portion can be slid from the connector to disconnect therefrom, and a locked configuration that maintains the proximal end portion in connection with the connector. In at least one embodiment, the quick release locking mechanism is biased toward the locked configuration.

In at least one embodiment, a radiopaque marker is provided on the distal end portion of the guidewire.

In at least one embodiment, an electromagnetic coil is provided at the distal end portion of the guidewire. Alternatively, a magnet, radiofrequency emitter or ultrasound crystal can be provided at the distal end portion of the guidewire.

An illuminating device is provided, including a distal end portion having an outside diameter configured and dimensioned to pass through an ostium of a sinus, at least one light emitting element in the distal end portion, and at least one structure extending from a proximal end of the device through the proximal end portion and at least part of the distal end portion to connect the at least one light emitting element with a power source.

In at least one embodiment, the illuminating device comprises an illuminating guidewire.

In at least one embodiment, the illuminating device comprises an ostium seeker device, and the distal end portion is rigid or malleable.

In at least one embodiment, the illuminating device comprises an ostium seeker device, and the distal end portion comprises a ball tip at a distal end thereof.

In at least one embodiment, the illuminating device comprises a sinus suction instrument, and the distal end portion further comprises a suction lumen configured and adapted to apply suction therethrough.

In at least one embodiment, the illuminating device comprises an integrated wire dilatation catheter, wherein an integrated illuminating guidewire extends distally of a distal end of a dilatation catheter of the device.

An illuminating guidewire device is provided including: a guidewire including an elongated main body having a flexible distal end portion and a relatively less flexible proximal end portion; at least one light conducting channel extending the length of the elongated body, and configured and dimensioned to deliver light from a proximal end of the guidewire to a distal end of the guidewire and to emit light from the distal end of the guidewire.

In at least one embodiment, the at least one light conducting channel comprises at least one illumination fiber.

In at least one embodiment, the at least one light conducting channel comprises at least two illumination fibers.

In at least one embodiment, the illumination fibers are formed of plastic.

In at least one embodiment, the at least one illumination fiber is formed of glass.

In at least one embodiment, the at least one light conducting channel comprises at least one laser fiber.

In at least one embodiment, a quick release connector is mounted over at least part of the proximal end portion of the elongated body, and is adapted to be connected to a light channel extending from a light source; and to quickly connect to and release from the proximal end portion of the elongated body.

In at least one embodiment, the quick release connector is optically coupled with the light source.

In at least one embodiment, a proximal end portion of the connector comprises a tapering light channel configured to adapt a relatively larger inside diameter of the light channel to a relatively smaller diameter of the proximal end of the elongated body.

In at least one embodiment, a proximal end portion of the quick release connector is adapted to connect with a light source. In at least one embodiment, the proximal end portion of the quick release connector includes an ACMI light post.

In at least one embodiment, the connector is rotatable with respect to the light channel extending from the light source, when the connector is connected to the light channel.

In at least one embodiment, the distal end portion of the connector comprises an opening configured to slidably receive the proximal end portion of the elongated body, and a quick release locking mechanism is configured to fix the proximal end portion received in the connector.

In at least one embodiment, the quick release locking mechanism, in a locked configuration, maintains a proximal end of the elongated body in alignment with a distal end of the tapering light channel of the connector.

In at least one embodiment, the quick release locking mechanism is movable between an unlocked configuration in which the proximal end portion can be slid from the connector to disconnect therefrom, and a locked configuration that maintains the proximal end portion in connection with the connector.

In at least one embodiment, a core support extends at least within the distal end portion of the elongated body of the guidewire. In at least one embodiment, the core support further extends within the proximal end portion.

An illuminating guidewire device is provided, including: a guidewire having an elongated main body with a flexible distal end portion and a relatively less flexible proximal end portion; a light emitting diode mounted in the distal end portion and configured to emit light from a distal tip of the distal end portion; and at least one electrical wire extending the length of the elongated body, being electrically connected to the light emitting diode, and extending proximally of a proximal end of the elongated body.

In at least one embodiment, the illuminating guidewire device includes at least two such electrical wires.

In at least one embodiment, a core support extends at least within the distal end portion of the elongated body. In at least one embodiment, the core support further extends within the proximal end portion.

In at least one embodiment, a radiopaque marker is provided on the distal end portion. In at least one embodiment, an electromagnetic coil is provided on the distal end portion.

An illuminating guidewire device is provided, including: a guidewire having a flexible distal end portion, a relatively less flexible proximal end portion, and a transparent portion interconnecting the distal and proximal end portions; a least one light emitting element mounted in the guidewire and configured to emit light through the transparent portion; and at least one structure extending from a proximal end of the device through the proximal end portion and connecting with the at least one light emitting element.

In at least one embodiment, the transparent portion comprises a clear tube.

In at least one embodiment, the clear tube includes cut out windows therein.

In at least one embodiment, the transparent portion comprises a plurality of struts interconnecting the proximal and distal end portions of the guidewire.

In at least one embodiment, a deflector is mounted distally of the at least one light emitting element in the transparent portion.

In at least one embodiment, a quick release connector is mounted over at least part of the proximal end portion, and is adapted to be connected to a light channel extending from a light source, and to quickly connect to and release from the proximal end portion of the guidewire.

In at least one embodiment, a core support extends at least within the distal end portion. In at least one embodiment, the core support further extends within the proximal end portion.

A quick release connector for use with an illuminating guidewire is provided to include: a main body having a proximal end portion and a distal end portion; a channel in the distal end portion and opening to a distal end of the main body, wherein the channel is configured and dimensioned to slidably receive a proximal end portion of the illuminating guidewire; and a quick release locking mechanism configured to assume a locked position and an unlocked position, wherein when in the locked position, the quick release locking mechanism fixes the proximal end portion of the illuminating guidewire in the channel.

In at least one embodiment, the quick release locking mechanism is biased to the locked position.

In at least one embodiment, upon inserting the proximal end portion of the illuminating guidewire into the channel, the proximal end portion contacts portions of the quick release locking mechanism, driving the portions apart to allow the proximal end portion to be slid into the channel.

In at least one embodiment, the quick release locking mechanism comprises a locking arm that extends into the channel and a portion that extends out of the housing, wherein the portion extending out of the housing is manually retractable to move the locking arm from the locked position to the unlocked position.

In at least one embodiment, the quick release locking mechanism includes at least two locking arms provided circumferentially about the distal end portion of the main body of the connector.

In at least one embodiment, the quick release locking mechanism comprises a pin vise.

In at least one embodiment, the proximal end portion of the connector is adapted to be connected to a light channel extending from a light source.

In at least one embodiment, the proximal end portion of the main body is optically coupled with a light source.

In at least one embodiment, the proximal end portion of the main body includes a tapering light channel configured to adapt a relatively larger inside diameter of a light channel to a relatively smaller diameter of the proximal end of the illuminating guidewire.

In at least one embodiment, the proximal end portion of the main body comprises an ACMI light post.

In at least one embodiment, the quick release connector is rotatable with respect to a light channel extending from a light source, when the connector is connected to the light channel.

These and other advantages and features of the invention will become apparent to those persons skilled in the art upon reading the details of the devices, methods and systems as more fully described below.

BRIEF DESCRIPTION OF THE DRAWINGS

FIG. 13A illustrates an illuminating guidewire device including a quick release connector that is optically coupled to a light source.

FIG. 13B is a view of the arrangement of FIG. 13A in which the quick release locking mechanism is in the locked position.

FIG. 14A illustrates an alternative quick release connector.

FIG. 14B illustrates the connector of FIG. 14A mounted over a proximal end portion of an illuminating guidewire.

FIG. 18 shows an illuminating guidewire having been extended distally of the limit of illumination of the scope, to effectively extend the illumination distance viewable by the scope.

DETAILED DESCRIPTION OF THE INVENTION

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a tube" includes a plurality of such tubes and reference to "the shaft" includes reference to one or more shafts and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
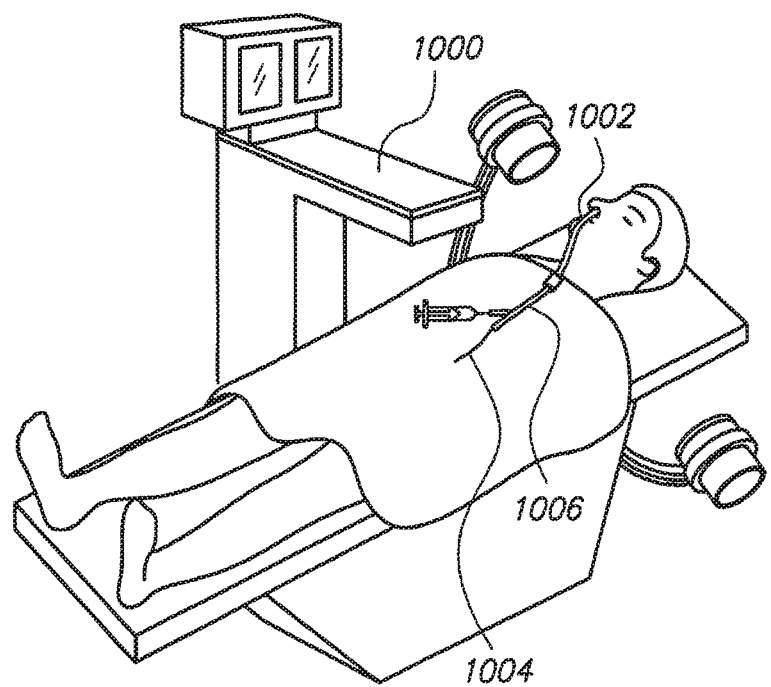
FIG. 1 is an illustration of a patient being treated by a system for catheter-based minimally invasive sinus surgery according to prior art techniques.

Turning now to FIG. 1, an illustration of a patient being treated by a system for catheter-based minimally invasive sinus surgery according to prior art techniques is shown. A C-arm fluoroscope 1000 that is useable to visualize a first introducing device 1002 (e.g., a sinus guide, guide catheter or guide tube), a second introducing device 1004 (e.g., a guidewire or elongated probe) and a working device 1006 (e.g., a balloon catheter, other dilatation catheter, debrider, cutter, etc.). The sinus guide, guide catheter or guide tube 1002 may be introduced under direct visualization, visualization provided by fluoroscope 1000 and/or from endoscopic visualization, to place the distal end of catheter or tube 1002 at a location approaching an ostium of a sinus to be treated.

Next guidewire or elongated probe 1004 is inserted through catheter or tube 1002 and distally advanced to extend the distal end of guidewire or elongated probe through the ostium to be treated and into the sinus that the ostium opens to. Proper placement often involves advancement and retraction of the distal end of guidewire or elongated probe, under fluoroscopic visualization, until it has been visually confirmed that the distal end of the guidewire or elongated probe is located where the surgeon believes the appropriate sinus to be located, relative to the other features of the patient's head that are visualized under fluoroscopy.

Once guidewire or elongated probe 1004 has been properly placed, working device 1006 is next passed over the guidewire or elongated probe 1006, under visualization via fluoroscope 1000 and/or an endoscope (not shown) that has been inserted adjacent catheter or tube 1002, to place the working end of working device 1006 in the target location where a surgical procedure is to be performed. Typically, the guidewire or elongated probe remains in place during the procedure. Under the same type(s) of visualization, the working (distal) end of working device is then actuated to perform the desired surgical procedure. In the case of a dilatation catheter, the balloon at the distal end portion of catheter 1006 is expanded once it has been located across the ostium. This expansion acts to open the ostium to allow proper mucus flow, as was described in more detail above.

After performance of the desired surgical procedure, the working device 1006 is deactivated and withdrawn from the patient, after which the remaining devices are withdrawn to complete the procedure.

By using the devices and methods described herein, at least the need for fluoroscopic visualization of the placement of the guidewire/elongated probe can be reduced or eliminated. Further optionally, all fluoroscopic visualization needs may be eliminated in some surgical circumstances.

It is to be appreciated that the devices and methods of the present invention relate to the accessing and dilatation or modification of sinus ostia or other passageways within the ear, nose and throat. These devices and methods may be used alone or may be used in conjunction with other surgical or non-surgical treatments, including but not limited to the delivery or implantation of devices and drugs or other substances as described in U.S. patent application Ser. No. 10/912,578, now U.S. Pat. No. 7,361,168, issued Apr. 22, 2008.

Figure 2A:
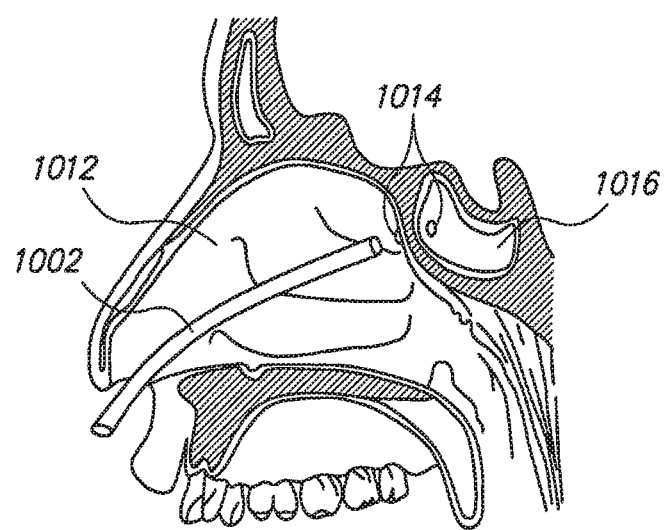
FIGS. 2A through 2D are illustrations of partial sagittal sectional views through a human head showing various steps of a method of gaining access to a paranasal sinus using a sinus guide.

FIGS. 2A through 2D are illustrations of partial sagittal sectional views through a human head showing various steps of a method of gaining access to a paranasal sinus using a sinus guide. In FIG. 2A, a first introducing device in the form of a sinus guide 1002 is introduced through a nostril and through a nasal cavity 1012 to a location close to an ostium 1014 of a sphenoid sinus 1016. Sinus guide 1002 may be straight, malleable, or it may incorporate one or more preformed curves or bends as further described in U.S. Patent Publication Nos. 2006/0004323; 2006/0063973; and 2006/0095066, now U.S. Pat. No. 7,462,175, issued Dec. 9, 2008, for example, each of which are incorporated herein, in their entireties, by reference thereto. In embodiments where sinus guide 1002 is curved or bent, the deflection angle of the curve or bend may be in the range of up to about 135 degrees.

Figure 2B:
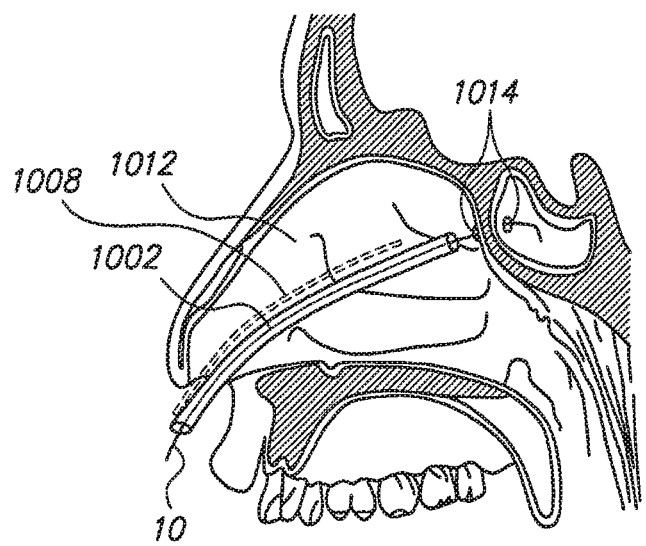

In FIG. 2B, a second introduction device comprising a guidewire 10 is introduced through the first introduction device (i.e., sinus guide 1002) and advanced so that the distal end portion of guidewire 10 enters the sphenoid sinus 1016 through the ostium 1014.

Figure 2C:
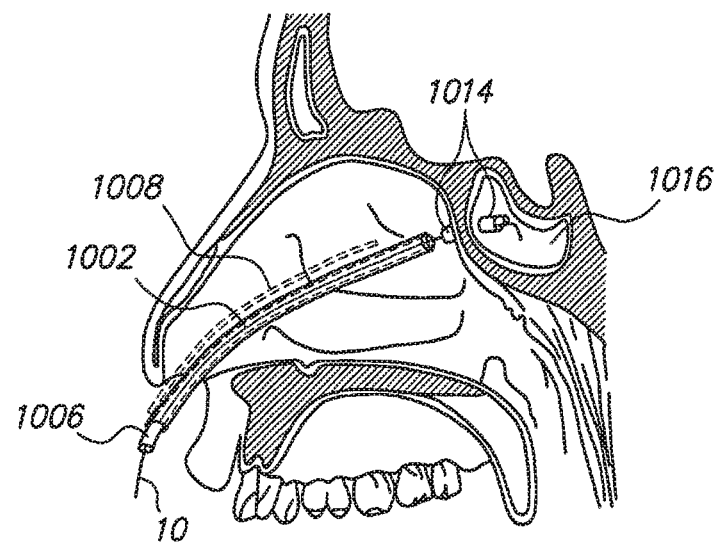
Figure 2D:
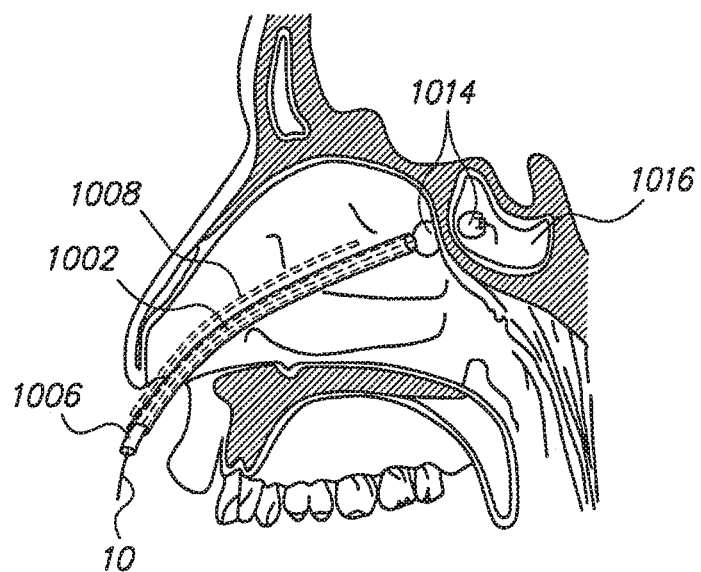

In FIG. 2C, a working device 1006, for example a balloon catheter, is introduced over guidewire 10 and advanced to extend the distal end portion of device 1006 into the sphenoid sinus 1016. Thereafter, in FIG. 2D, working device 1006 is used to perform a diagnostic or therapeutic procedure. In this particular example, the procedure is dilatation of the sphenoid sinus ostium 1014, as is illustrated in FIG. 2D, where the balloon of device 1006 is expanded to enlarge the opening of the ostium 1014. After completion of the procedure, sinus guide 1002, guidewire 10 and working device 1006 are withdrawn and removed. It will be appreciated that the present invention may also be used to dilate or modify any sinus ostium or other man-made or naturally occurring anatomical opening or passageway within the nose, paranasal sinuses, nasopharynx or adjacent areas. As will also be appreciated by those of ordinary skill in the art, in this or any of the procedures described in this patent application, the operator may additionally advance other types of catheters, and that guidewire 10 may be steerable (e.g. torquable, actively deformable) or shapeable or malleable.

FIGS. 2B-2D show an optional scope 1008 in dotted lines, that may be inserted to provide visualization of advancement of sinus guide 1002 and/or inserted alongside catheter 1002 to provide visualization of all or at least a portion of working tool 1006. It is to be appreciated that optional scope 1008 may comprise any suitable types of rigid or flexible endoscope and such optional scope may be separate from or incorporated into the working devices and/or introduction devices of the present invention, as further described in provisional Application Ser. No. 60/884,874 titled "Endoscopic Methods and Devices for Transnasal Procedures," filed Sep. 15, 2006, and which is hereby incorporated herein, in its entirety, by reference thereto.

Although scope 1008 may be useful to reduce or eliminate the need for fluoroscopic visualization during placement of sinus guide 1002 and/or for visualization of the procedure performed by working device 1006, it does not provide stand-alone capability to see inside the sinus (e.g., sphenoid sinus 1016 or other sinus of interest), and therefore cannot provide sufficient visual feedback for use in guiding guidewire 10 into the desired sinus (e.g., frontal sinus, or some other sinus of interest) or sufficient visual image confirmation of correct placement of guidewire 10 into the desired sinus.

Figure 3:
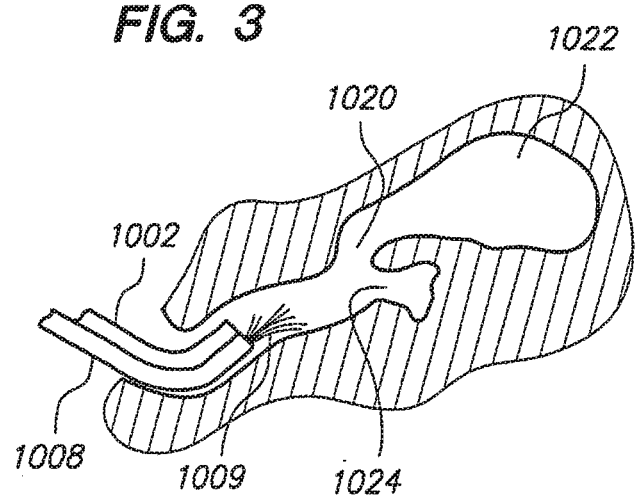
FIG. 3 illustrates a scope introduced on the side of the sinus guide.

Further, depending upon the particular configuration of the sinus passageways to be traversed to gain access to a target ostium, the scope 1008, due to physical limitations (e.g., outside diameter, degree of rigidity, etc.) may be unable to visualize as deep as the location of the ostium of interest. For example, FIG. 3 illustrates a situation where scope 1008 has been inserted as far as possible without causing significant trauma to the patient. The range of adequately illuminated visibility in this case does not extend all the way to ostium 1020, as indicated schematically by the rays 1009 shown extending distally from scope 1008. In this case, adequately illuminated visualization of guidewire 10 into ostium 1020 would not be possible via scope 1008. Additionally, if sinus guide 1002 is physically capable of being extended further distally to place the distal end thereof at the approach to ostium 1020, scope 1008 would also not be capable of adequately visualizing this. Thus, prior to the current invention, fluoroscopic or other x-ray visualization of these procedures was required, in order to ensure that the devices approach (and extend through) the appropriate ostium 1020 and not another adjacent opening, such as opening 1024.

In order to overcome these and other problems, the guidewire devices 10 of the present invention include their own light emitting capability. By illuminating a distal end portion of guidewire 10, a process known as transillumination occurs as guidewire 10 traverses through the sinus passageways, passes through an ostium and enters a sinus cavity. Transillumination refers to the passing of light through the walls of a body part or organ. Thus, when guidewire 10 is located in a sinus, the light emitted from guidewire 10 passes through the facial structures and appears as a glowing region on the skin (e.g., face) of the patient. It is noted that the light emitted from scope 1008, such as positioned in FIG. 3, for example, results in transillumination as well, but the resultant glow is much more diffuse and larger in area. As the light source in guidewire 10 gets closer to the surface of the structure that it is inserted into (e.g., the surface of the sinus), the transillumination effect becomes brighter and more focused (i.e., smaller in area). Additionally, the movements of the guidewire 10 can be tracked by following the movements of the transillumination spot produced on the skin of the patient.

Figure 4:
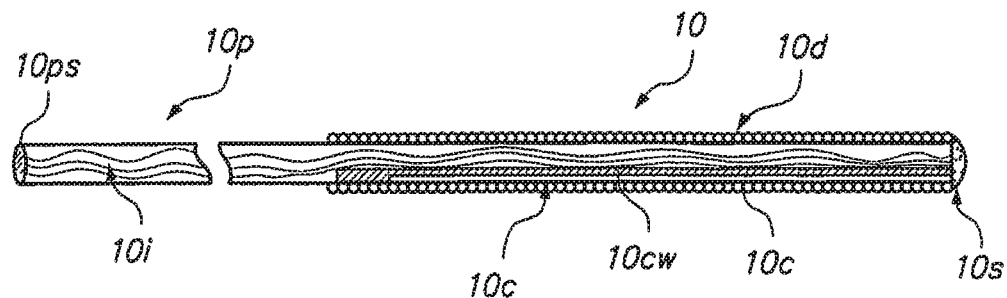
FIG. 4 shows an illuminating guidewire according to one embodiment of the present invention.

FIG. 4 shows an illuminating guidewire 10 according to one embodiment of the present invention. Device 10 includes a flexible distal end portion 10*d* that provides a similar degree of flexibility to a standard, non-illuminating type of guidewire. Distal end portion 10*d* may include a coil 10*c* as an exterior portion thereof, to help provide the desired flexibility to this portion. The proximal end portion 10*p* of device 10 extends the device to provide a sufficient length so that device 10 extends proximally out of the patient (and, when inserted through another device, such as a sinus guide, proximally out of the device into which guidewire 10 is inserted), at all times, including the deepest location into which the distal end of device 10 is placed. The proximal end portion 10*p* can have visible markings, preferably spaced at equal intervals, that can be observed by the user to confirm how far the guidewire 10 has been placed in the patient. Proximal end portion 10*p* also provides the necessary mechanical properties required to make the guidewire function properly. These mechanical properties include torquability, i.e., the ability to torque the proximal end portion 10*p* from a location outside of the patient and have that torque transmitted to the distal end portion 10*p*; pushability, i.e., sufficient rigidity, so that when an operator pushes on the proximal end portion 10*p* from a location outside of the patient, the pushing force transmits to the distal portion 10*d* to advance the distal portion 10*p* without buckling the device 10; and tensile strength so that an operator can pull on the proximal end portion 10*p* from a location outside of the patient and withdraw device 10 from the patient without significant plastic deformation or any disintegration of the device.

Coil 10*c* may be formed from a stainless steel wire, for example. The diameter of the coil wire can be between about 0.004 and about 0.008 inches, typically about 0.006 inches. Alternative materials from which coil 10*c* may be formed include, but are not limited to: ELGILOY®, CONICHROME® or other biocompatible cobalt-chromium-nickel alloy; nickel-titanium alloys, or other known biocompatible metal alloys having similar characteristics. Further alternatively, distal end portion may comprise a braided metallic construction of any of the aforementioned materials in lieu of a coil.

The external casing of the proximal portion 10p can be made from a polyimide sheath, a continuous coil (optionally embedded in polymer or having polymer laminated thereon), a hypotube (e.g., stainless steel hypotube), a laser-cut hypotube, a cable tube, or a tube made from PEBAX® (nylon resin) or other medical grade resin. In any of these cases the construction needs to meet the required torquability, pushability and tensile requirements of the device.

In the example shown, coil 10c is joined to proximal portion 10p by solder, epoxy or other adhesive or mechanical joint. One or more illumination channels 10i are provided in device 10 and extend the length thereof. Illumination channels 10i are configured to transport light from the proximal end of device 10 to and out of the distal end of device 10. In the example shown, two illumination channels are provided, each comprising a plastic illumination fiber. The plastic used to make the illumination fibers is compounded for light transmission properties according to techniques known and available in the art. As one example, ESKA™ (Mitsubishi Rayon), a high performance plastic optical fiber may be used, which has a concentric double-layer structure with high-purity polymethyl methacrylate (PMMA) core and a thin layer of specially selected transparent fluorine polymer cladding. In one example, illumination fibers each have an outside diameter of about 0.010". The illumination fibers can have an outside diameter in the range of about 0.005 inches to about 0.010 inches. Alternatively, a single plastic illumination fiber 10i may be used that has an outside diameter of about 0.020". Further alternatively, glass illumination fibers may be substituted which are much smaller in outside diameter, e.g., about 0.002". In this case, more illumination fibers may be provided in a bundle, e.g., about six to fifty glass fibers 10i may be provided.

The distal end of device 10 is sealed by a transparent (or translucent) seal 10s which may be in the form of epoxy or other transparent or translucent adhesive or sealing material. Seal 10s maintains the distal ends of illumination fibers 10i coincident with the distal end of device 10 and also provides an atraumatic tip of the device 10. Further, seal 10s prevents entrance of foreign materials into the device. The distal end can be designed to either focus or distribute the light as it emanates therefrom, to achieve maximum transillumination effects. In this regard, the distal end can include a lens, prism or diffracting element.

The proximal end of device 10 is also sealed by a transparent (or translucent) seal 10ps which may be in the form of epoxy or other transparent or translucent adhesive or sealing material. Seal 10ps maintains the proximal ends of illumination fibers 10i coincident with the proximal end of device 10. The proximal end of device 10 maybe further prepared by grinding and polishing to improve the optical properties at the interface of the proximal end of device 10 with a light source. The illumination fibers 10i at locations intermediate of the proximal and distal ends need not be, and typically are not fixed, since no mapping of these fibers is required, as device 10 provides only illumination, not a visualization function like that provided by an endoscope. Further, by leaving illumination fibers free to move at locations between the proximal and distal ends, this increases the overall flexibility and bendability of device 10 relative to a similar arrangement, but where the illumination fibers 10i are internally fixed.

The outside diameter of device 10 may be in the range of about 0.025 inches to about 0.040 inches, typically about 0.030 to 0.038 inches, and in at least one embodiment, is about 0.035"±0.005". At least the distal portion 10p of device 10 is provided with a core support 10cw that is contained therein. In the example shown in FIG. 4, core support 10cw is a wire that is fixed to proximal section 10p such as by laser welding, epoxy or other adhesive or mechanical fixture. Core support 10cw may extend substantially the full length of device 10. In any case, core support 10cw is typically formed from stainless steel NITINOL (nickel-titanium alloy) or other biocompatible nickel-titanium alloys, cobalt-chromium alloys, or other metal alloys that are biocompatible and provide the necessary rigidity and torquability. Core support 10cw may be formed as a wire, as in the example shown in FIG. 4, or alternatively, may be braided from any of the same materials or combination of materials mentioned above. Core support 10cw, when formed as a wire can be ground to different diameters to provide varying amounts of rigidity and torquability. When formed as a braid, the braid can be formed to have varying amounts of rigidity and torquability along the length thereof. For example, core wire 10cw has a larger outside diameter at the proximal end portion than at the distal end portion so that it is more rigid and transfers more torque from the proximal portion of device 10, whereas at the distal end portion, core 10cw is relatively more flexible and twistable. For core supports 10cw that extend through proximal portion 10p, the portion of core support near the proximal end of device 10 may have an even larger outside diameter.

Figure 5:
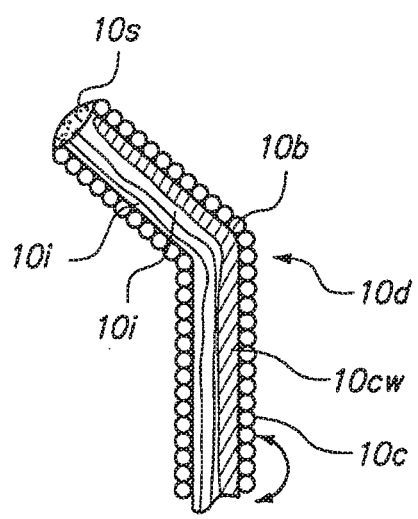
FIG. 5 shows a distal end portion of a guidewire having a bent shape.

Core support 10cw particularly increases the pushability and the torquability of coil 10c which, by itself, is quite flexible and twistable. Combined with the core support 10cw, the distal portion is much more effective at transferring pushing and torquing forces without buckling or twisting. Additionally, core support 10cw may be plastically deformed or memory set into a bent shape, an example of which is shown in FIG. 5. Bend 10b provides a steerability function, allowing an operator to direct the distal end of device 10 in different directions by torquing device about the longitudinal axis of the device, as indicated by the arrows in FIG. 5. In some embodiments this bending can be performed by an operator in the midst of a procedure, which can be particularly useful in combination with a scope 1008, as viewing through the scope may make it apparent to the operator that the guidewire 10 needs to be inserted or directed at an angle offset from where the straight direction along the longitudinal axis of the device would direct it to. In some embodiments, the guidewire 10 does not have a core support or core wire. In these embodiments, the outer jacket (e.g., a coil, cable tube, laser-cut hypotube, braided polymer tube, etc.) provides the support for torque, pushability and tension. An advantage of not having a core wire/core support is that the full inner diameter of the guidewire is then available to be filled with illumination fibers.

Figure 6:
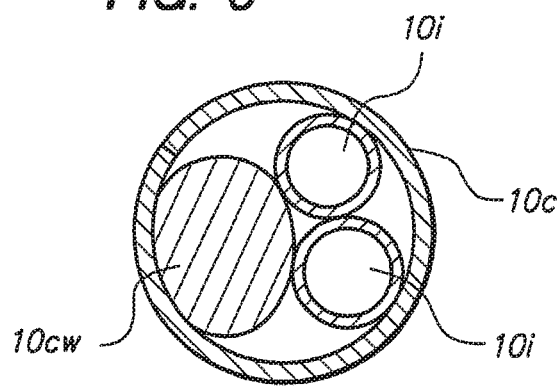
FIG. 6 is a cross-sectional illustration of a distal end portion of a guidewire device showing a core support fixed to the coil.

The illumination fibers, as noted above, can be free to move about radially within the device. Further, there is no need to center the illumination fibers 10i with respect to device 10 even at the distal and proximal ends of the device. FIG. 6 is a sectional illustration of a distal end portion of device 10 showing core support 10cw fixed to coil 10c, with illumination fibers 10i residing adjacent to core support 10cw, but not fixed to either core support 10cw or coil 10c.

Figure 7:
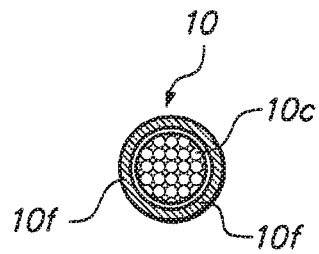
FIG. 7 shows a cross-sectional view of a guidewire device that includes a fiber optic bundle of light fibers.

The plastic or glass illumination fibers 10i of the device shown in FIG. 4 are typically used to transmit light from a light source such as one provided in a operating room for use by endoscopes, e.g., xenon light source, halogen light source, metal halide light source, etc. Alternatively, device 10 may be configured to transmit light from other light sources, such as a laser light source, wherein laser fibers 10f would be substituted for the illumination fibers described above, and extend through device 10 in a fiber optic bundle as illustrated in the cross-sectional view of FIG. 7. The fiber optic bundle, like the illumination fibers 10*i*, contributes to stiffness (in both bending and torquing motions) of device 10, thereby enhancing trackability, steering and other torquing.

Figure 8:
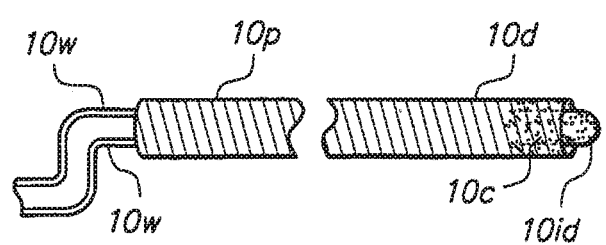
FIG. 8 shows an illuminating guidewire according to another embodiment of the present invention.

FIG. 8 illustrates another embodiment of an illuminating guidewire 10. In this example, proximal end portion of device 10 is formed externally by a coil with a polymer layer laminated thereon, but any of the other arrangements described above may be substituted. In this example, illumination is provided by a high intensity light emitting diode (LED) 10*id* fitted at the distal end of device 10. The proximal end of device 10 may be sealed such as with epoxy, or any of the other alternatives mentioned above with regard to the proximal end of device 10 in FIG. 4, in order to prevent pulling on the wires 10*iw* at the connections with LED 10*id*, as well as to seal the proximal end of the device. Grinding and polishing are not necessary, as the proximal end of device 10 in FIG. 8 does not transmit light.

Figure 9:
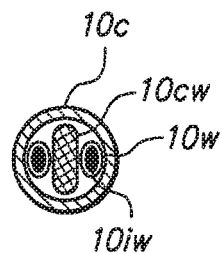
FIG. 9 is a cross-sectional illustration of a distal end portion of the guidewire shown in FIG. 8.

Device 10 in FIG. 8 performs substantially similar to the device 10 of FIG. 4 with regard to the properties of pushability, torquability and tensile properties. Device 10 of FIG. 8, however, does not require illumination fibers or laser fibers. Instead, a pair of insulated lead wires are electrically connected to the terminals of LED 10*id* (not shown) and then extend within device 10 over the length of device 10 to extend proximally from the proximal end of device 10. The free ends of wires 10*w* are configured to be connected to a power source that functions as the source of electrical power, to deliver electrical energy to LED 10*id* to illuminate it. FIG. 9 illustrates a cross-sectional view of a distal end portion of device 10 of FIG. 8. In this example, core support 10*cw* is in the form of a flattened distal end core wire or shaping ribbon as known in the art, that extends between the two wires 10*w*. FIG. 9 also illustrates the insulation layer 10*iw* over each wire.

Any of the devices 10 described herein may optionally include one or more radiopaque markers and/or electromagnetic coils on the tip of the device 10 and/or elsewhere along the device for enhancing visibility by fluoroscopy systems, image guided surgery (IGS) systems, or other visualization systems.

Figure 10:
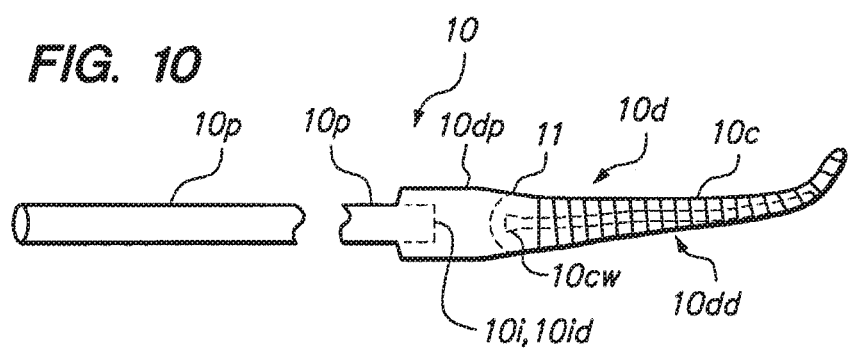
FIG. 10 shows an illuminating guidewire according to another embodiment of the present invention.
Figure 11:
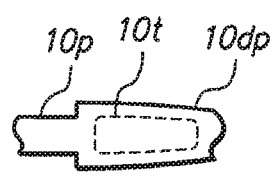
FIG. 11 illustrates an alternative transparent portion that may be included in a device shown in FIG. 10.

FIG. 10 shows an alternative design of device 10 in which light is emitted proximally of the distal end of the device. This configuration may employ any of the various light transmission means described above (e.g., illumination fibers, laser fibers, LED). The proximal portion 10*p* may be constructed in any of the manners described above with regard to other embodiments of device 10. The distal portion 10*d* includes a transparent proximal end portion 10*dp* that mounts over the distal end of proximal end portion 10*p* of the device 10. The transparent portion 10*dp* permits the illumination emitted from illumination member 10*i* or 10*id* to pass out of the device 10 at the location of transparent portion 10*dp*. The illumination member(s) 10*i* or 10*id* thus terminate at the proximal end portion 10*dp* of the distal end portion of device 10. Distally of this transparent portion 10*dp*, the distal portion 10*dd* of distal end portion 10*d* of device 10 extends as a floppy guidewire leader or tip. This floppy guidewire leader or tip 10*dd* may include a coiled section 10*c* and may optionally include a core support 10*cw* in the manner described above with regard to FIG. 4. The light emitted from illumination fibers will disperse naturally through the transparent portion 10*dp*. Optionally, a deflector 11, such as a convex mirror (e.g., parabolic or other convex) shape or other reflective surface may be provided distally of illumination fibers/light emitting portion 10*i*, 10*id* of device 10 to deflect light rays out of the transparent portion. Additionally, or further alternatively, illumination fibers 10*i* may be angled at the distal end portions thereof to direct the emitted light out through the transparent portion.

This configuration may be beneficial in further protecting the illumination emitter(s) 10*i*, 10*id* from foreign materials inside the body, as well as from trauma that may be induced by bumping the illumination emitter up against structures within the body. Further, a floppy guidewire leader 10*dd* of this type may provide more flexibility and maneuverability than a device in which the illumination emitter is located on the distal tip of the device.

Figure 12:
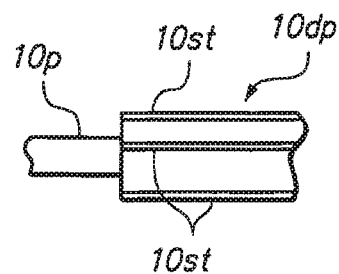
FIG. 12 illustrates another alternative transparent portion that may be included in a device shown in FIG. 10.

Transparent portion 10*dp* may be provided as a clear plastic or glass integral tube, or may have openings or windows 10*t* provided therein (see the partial view of FIG. 10). Further alternatively, transparent portion may be formed by a plurality of struts 10*st* circumferentially arranged to interconnect the distal floppy tip 10*dd* with the proximal end portion 10*p* of device 10 as shown in the partial illustration of FIG. 12. Alternatively members 10*st* may be intersecting in a criss-crossing cage like configuration or other cage configuration. In any of these alternative configurations, members 10*st* may be transparent, but need not be and could be formed of non-transparent materials, such as metals or opaque plastics, for example.

Device 10 should be readily connectable to and disconnectable from a power source to enable attachment for providing illumination for positioning the guidewire 10 and/or other devices during a procedure, detachment to allow another device to be slid onto the guidewire 10 from a free proximal end thereof, and reattachment to again provide illumination, to assist in guidance/visualization of the device being passed over the guidewire 10, for example.

FIGS. 13A and 13B illustrate one example of a coupler 20 that is configured for quick connection and disconnection of an illumination guidewire 10 that employs illumination fibers 10*i* or laser fibers 10*f*. Coupler 20 is connected to a light source 1030, such as a conventional endoscope light source, for example, or other light source capable of delivering preferably at least 10,000 lux through coupler 20. Light cable 1032 optically connects connector 20 with light source 1030 to deliver light from the light source 1030 to connector 20. Light cable 1032 can optionally be a fluid-filled light cable, such as the type provided with DYMAX BlueWave™ 200 and ADAC Systems Cure Spot™ light cables, for example. A liquid filled light cable comprises a light conducting liquid core within plastic tubing. The liquid is non-toxic, non-flammable and transparent from 270 to 720 nm. The ends of a liquid filled light cable can be sealed with high quality quartz glass and metal spiral tubing surrounded by a plastic sleeve for exterior protection.

Connector 20 includes a proximal channel, slot or bore 22 that has an inside dimension or circumference that is slightly greater than the outside diameter or circumference of device 10 at the proximal end portion 10*p*. A quick release locking mechanism 24 is provided for locking and unlocking device 10 within connector 20. Quick release locking mechanism is biased toward the locking position shown in FIG. 13B, in which the locking portion 24*a* of mechanism 24 is driven into channel slot or bore 22 and may even abut against the opposite wall of the channel, slot or bore 22, when no guidewire 10 has been inserted. Locking mechanism 24 may be spring-biased toward the locked position, for example. Additionally, locking mechanism 24 may include a ball and detent arrangement, or other temporary locking means to maintain the mechanism 24 in the locked configuration. An additional, similar mechanism may be provided to temporarily fix locking mechanism 24 in the unlocked configuration shown in FIG. 13A. Alternative locking mechanisms may be employed, such as a pivoting lock arm, for example, that is manually pivotable between the locked and unlocked orientations, or other mechanism that would be apparent to one of ordinary skill in the mechanical arts, such as a collapsible silicone valve that grips the device, for example.

Light cable 1032 generally has a much larger inside diameter than the inside diameter or combined inside diameters of the illumination fibers 10i. Accordingly, the proximal end portion of connector 20 provides a tapering or funnel shaped pathway 26 having a proximal inside diameter that is substantially equivalent to the inside diameter of cable 1032 or greater, and which tapers to a distal inside diameter that is about the same or only slightly greater than the inside diameter or combined inside diameters of the illumination fiber(s), or alternatively, that is about the same or only slightly greater than the outside diameter of the proximal end of device 10. The light cable 1032 generally has a larger diameter bundle of illumination fibers than that contained within the illuminating guidewire 10. Accordingly, the tape 26 is used to transition between the larger bundle in the light cable 1032 and the smaller bundle in the guidewire 10. With this arrangement, light delivered through light cable 1032 is concentrated or focused down to a pathway where most of the light can be transmitted through the illumination fibers.

To insert device 10 into connector 20, an operator retracts quick connect locking mechanism 24 to the open position shown in FIG. 13A. If quick connect mechanism 24 is provided with a temporary locking mechanism as referred to above, then quick connect locking mechanism 24 can be temporarily fixed in the orientation shown in FIG. 13A, without the operator having to hold it open. Otherwise, the operator will hold connector 24 open in the position shown in FIG. 13A. The proximal end of device 10 is next inserted into the open channel, slot or bore 22 and slid proximally with respect to connector 20 until the proximal end of device 10 abuts against the proximal end of channel, slot or bore 22. Quick release mechanism is next released by the operator (in embodiments when there is no temporary locking mechanism to maintain the quick release in the open configuration) or released from the temporary locked open configuration, so that the locking arm 24a is advanced toward the proximal end portion 10p of device 10, by the biasing of quick connect locking mechanism 24 described above. Locking arm 24a contacts device 10 and holds device 10 under compression between locking arm 24a and the opposite inner wall of channel, slot or bore 22, with sufficient force to prevent device 10 from sliding out of connector 20 even if the distal tip of device 10 is pointed straight down in a vertical direction. Optionally, locking arm 24a may be additionally temporarily locked in place by a ball and detent mechanism, or other temporary locking mechanism, as mentioned above. To remove device 10 from connector 20, quick connect locking mechanism 24 is repositioned to the open or unlocked orientation shown in FIG. 13A and the device is slid distally with respect to the connector until it is free from the connector 20.

FIGS. 14A-14B illustrate an alternative connector 20 that includes a quick release locking mechanism 24. In this example, two or more locking arms 24 are provided circumferentially about the distal end of connector 20. Arms 24 are biased to the closed or locked configuration as shown in FIG. 14A. For example, arms 24 may be made from resilient spring steel, nickel-titanium alloy or resilient plastic and formed to assume the configuration shown in 14A when mounted to connector 20 and when in an unbiased state. Installation of device 10 into connector 20 is simplified by the automatic grasping and temporary locking functions provided by quick release locking mechanism 24. The proximal end of device 10 is simply inserted between the two or more arms 24. Arms 24 included ramped or cammed surfaces 24b that guide the proximal end of device 10 into connector 20, and, as device 10 is pushed against these surfaces 24b, arms 24 are deflected into the opened, biased configuration shown in FIG. 14B. The biasing/resiliency of arms 24 imparts compressive forces to the shaft of device 10 via temporary locking surfaces 24a, so that device 10 is gripped and held in position as shown in FIG. 14B. To remove device 10, the operator needed simply pull on device 10, while holding connector 20 relatively immobile, with a force sufficient to overcome the compressive and frictional forces imparted by surfaces 24a. The resilient arms 24 then return to the unbiased configuration shown in FIG. 14A. Optionally, surfaces 24a may be coated with, or include a friction enhancing surface, such as rubber or other elastomer, and/or be roughened, such as by knurling or other surface roughening technique.

In the example shown in FIGS. 14A-14B, the light cable 1032 that is provided has an inside diameter that is about the same as the diameter of the proximal end of device 10 and thus, no tapering channel 26 is required. However, for arrangements where the light cable 1032 is much larger, as is usually the case when using a conventional endoscope light source 1030, connector 20 may be provided with a tapering light channel 26 in the same manner as described above with regard to the embodiment of FIGS. 13A-13B.

Figure 15:
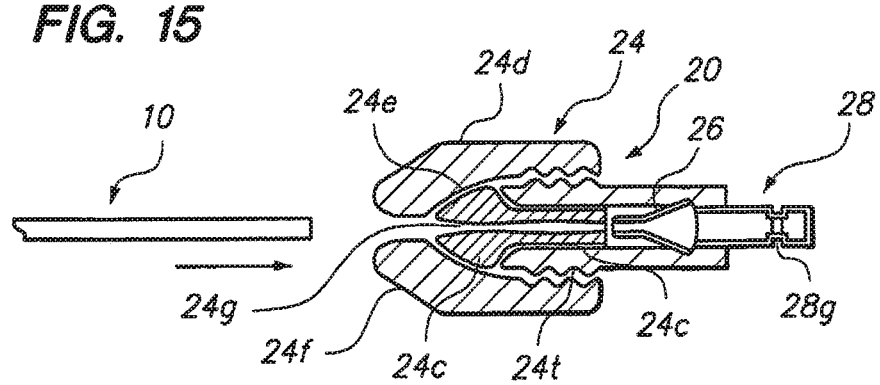
FIG. 15 illustrates another alternative quick release connector.

FIG. 15 illustrates a longitudinal sectional view of a connector 20 that is quickly connectable and releasable from a guidewire device 10 and is also connectable to and releasable from standard light source cables that are typically found in operating rooms. Thus, this connector 20 functions both as an adapter to connect to a conventional endoscope light source channel or cable, and as a quick release locking connector to connect to and release from a proximal end portion of guidewire 10.

The proximal end of connector 20 is provided with a light post 28 that is configured to mate with a connector on the distal end of a light cable extending from a conventional endoscope light source. For example, light post 28 may be an ACMI light post (ACMI Corporation) or other standard connector typically used to connect endoscopes to operating room light sources. Because the cable extending from an operating room light source generally has a much larger inside diameter than the inside diameter or combined inside diameters of the illumination fibers of device 10, and larger than the diameter of the proximal end of guidewire 10, the proximal end portion of connector 20 includes a light tapering or funnel-shaped pathway 26 like that described above with regard to FIG. 13A.

The quick release locking mechanism 24 in this example includes a collet 24c that is configured to center the proximal end of device 10 with the distal end of tapering pathway 26. A threaded cap 24d is threaded over mating threads 24t on the body of connector 20, so that when cap 24d is torqued in a direction to advance cap 24d proximally with respect to the body of connector 20, inner ramped or cammed surfaces 24e of cap 24d ride over outer ramped or cammed surfaces 24f of collet 24c, thereby functioning as a pin vise and clamping collet 24c against the proximal end portion of device 10 to clamp and maintain device 10 in its current position relative to connector 20. To insert device 10, cap 24*d* is rotated in a reverse direction from that described above to open the distal opening of the inner channel 24*g* of collet 24*c* to a dimension larger than the outside diameter of the proximal end of device 10, so that device 10 can be easily slid through the channel 24*g* until the proximal end of device 10 abuts the proximal end portion of collet 24*c*, or approximates the same. The cap 24*d* is then turned with respect to the body of connector 20 to clamp device 10 into position, as described above. Removal of device 10 can be performed by turning cap 24*d* in a reverse direction relative to connector body 20, thereby loosening the grip of collet 24*c* on device 10, after which device 10 can be easily slid out from connection with connector 20. Components of connector 20 may be made from metal, such as stainless steel or other biocompatible metals, or temperature-resistant thermosetting polymer, for example.

Figure 16:
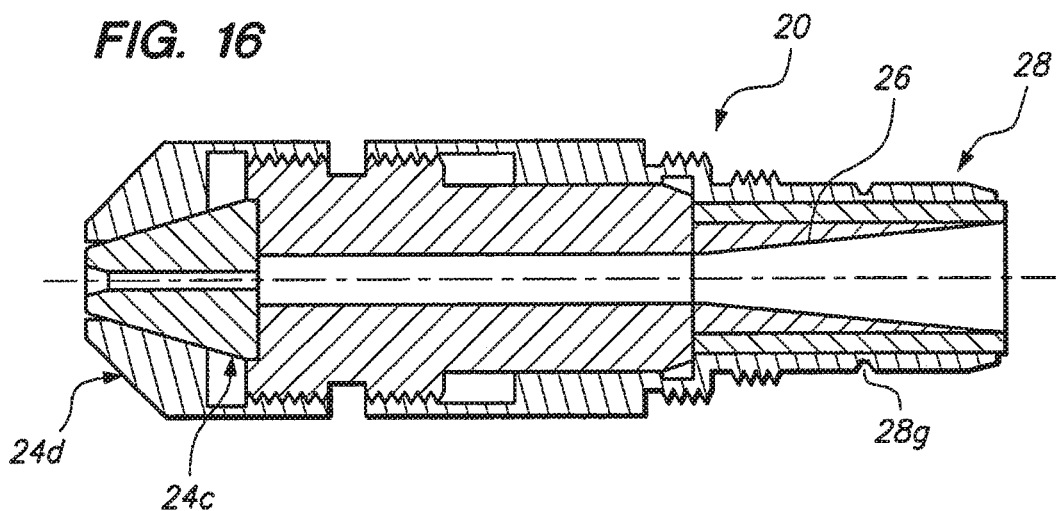
FIG. 16 illustrates another alternative quick release connector.

Light post 28 is rotatable with respect to the light cable 1032 of the light source 130 when connector 20 is connected to the distal end connector of the light cable 1032. This allows device 10, when connected to connector 20 in this arrangement, to be rotated during use without building up significant twisting or rotational counter forces within the light cable 1032. For example, in the light post 28 shown, the female receptacle (not shown) of the light cable 1032 couples over light post 28 and engages in groove 28*g*, about which the female receptacle is then rotatable relative to light post 28. FIG. 16 is a longitudinal sectional view of a connector 20 that is similar to the connector 20 described with regard to FIG. 15 above. One difference in the example of FIG. 16 is that the tapered light guide 26 is provided in the light post 28, as contrasted with being provided in the proximal end portion of the main body of connector 20 in FIG. 15. However, in both cases, the function is the same.

Turning now to FIGS. 17A-17E, illustrations of partial coronal sectional views through a human head showing various steps of a method for treating an ostium that opens to a frontal sinus are shown. The methods described here, and all other methods disclosed herein may also comprise a step of cleaning or lavaging anatomy within the nose, paranasal sinus, nasopharynx or nearby structures including but not limited to irrigating and suctioning. The step of cleaning the target anatomy can be performed before or after a diagnostic or therapeutic procedure. The methods of the present invention may also include one or more preparatory steps for preparing the nose, paranasal sinus, nasopharynx or nearby structures for the procedure, such as spraying or lavaging with a vasoconstricting agent (e.g., 0.025-0.5% phenylephyrine or Oxymetazoline hydrochloride (Neosynephrine or Afrin) to cause shrinkage of the nasal tissues, an antibacterial agent (e.g., provodine iodine (Betadine), etc. to cleanse the tissues, etc.

Figure 17A:
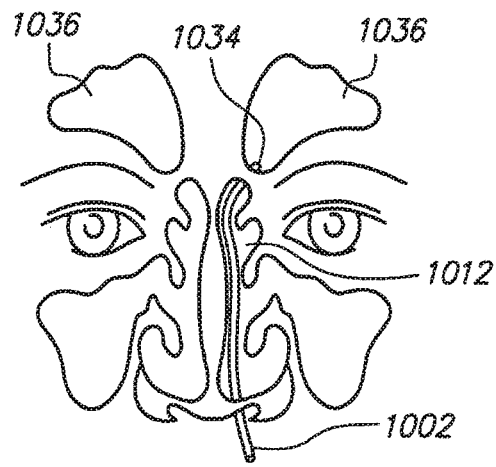
FIGS. 17A-17E are illustrations of partial coronal sectional views through a human head showing various steps of a method for treating an ostium that opens to a frontal sinus.

In FIG. 17A, a first introducing device in the form of a sinus guide 1002 is introduced through a nostril and through a nasal cavity 1012 to a location close to an ostium 1034 of a frontal sinus 1036. Sinus guide 1002 may be as described previously herein, or as described in the applications incorporated herein by reference. The advancement of sinus guide 1002 can be visualized with a scope inserted into the nasal cavity 1012 and advanced as close to the ostium 1034 as possible without causing significant trauma to the tissues therein.

Figure 17B:
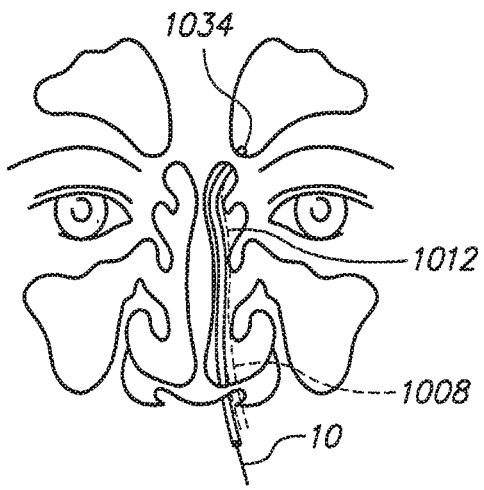

Once the surgeon is satisfied that the distal end of the sinus guide 1002 is positioned close enough to the appropriate ostium 1034, illuminating guidewire 10, connected to a light source as described by any of the techniques mentioned above, is inserted through sinus guide 1002 and advanced therethrough, see FIG. 17B. There may be some transillumination from the light emitted from the scope which can be used to confirm that the sinus guide 1002 is positioned in the correct general area, which confirmation can be made even before the distal tip of guidewire 10 exits the distal end of sinus guide 1002. However, much more specific transillumination effects are produced when the tip of guidewire 10 exits the distal end of guide 1002 and especially when the light emitting portion of guidewire 10 touches or approximates an intended target surface, such as an inner wall of a sinus, for example. As the guidewire 10 is advanced, transillumination on the face of the patient can be observed as a glowing spot that moves as the distal end portion of device 10 moves, thereby making it possible to visibly track the location of the light emitting portion of device 10 without the need to use radiographic imaging, such as by fluoroscopy, for example.

Figure 17C:
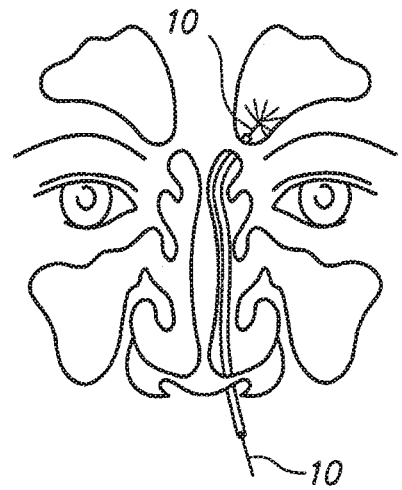
Figure 17D:
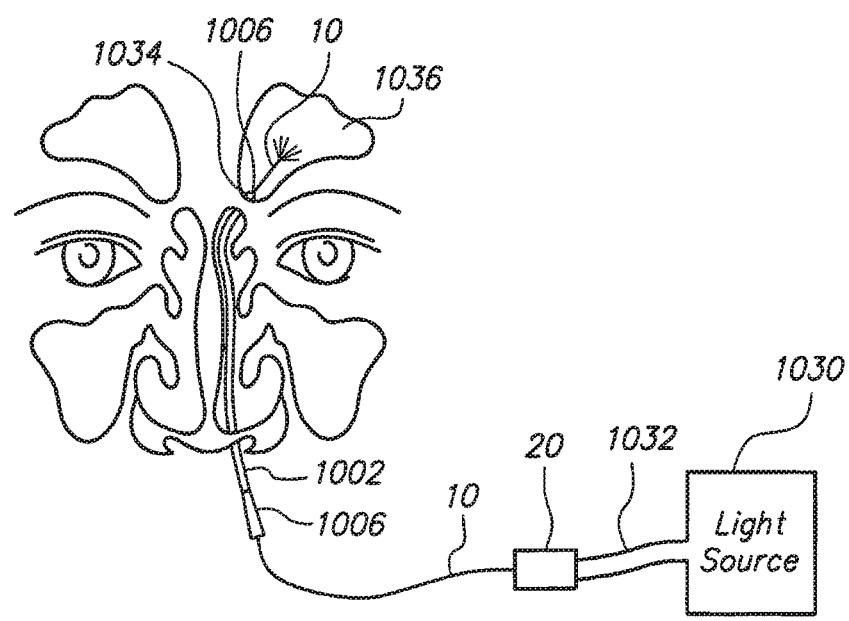
Figure 17E:
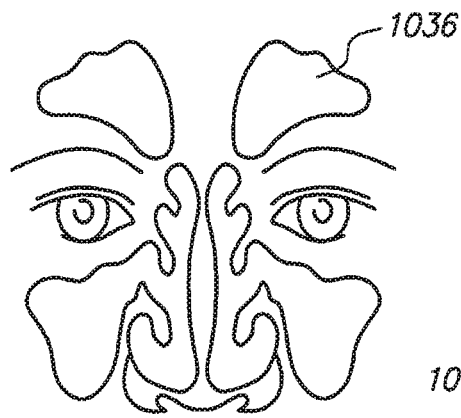

While there may be some diffuse transillumination on the forehead of the patient overlying the frontal sinus 1036 as the light emitting portion of device 10 approaches the ostium 1034, the glow on the forehead becomes brighter and smaller in dimension (more focused) as the light emitting portion passes through the ostium 1034 and enters the frontal sinus 1036, FIG. 17C. As device 10 is further advanced, the glowing spot becomes most defined and brightest as the light emitting portion approaches and contacts a wall of the frontal sinus 1036. Further, as noted, the movement of the transilluminated spot can be visibly followed to confirm that the guidewire 10 is indeed moving within the location of the frontal sinus, as can be confirmed by the surgeon's knowledge of the particular anatomy of the patient being treated. In this regard, a CAT scan or other image of the sinus anatomy can be performed prior to this procedure and studied by the surgeon, to apprise the surgeon of any distinctive or unusual patterns in the individual patient's sinus anatomy which might be useful in tracking and confirmation of where the guidewire is located, as indicated by the transillumination.

Once properly positioned, the proximal end of device 10 is disconnected from connector 20, while leaving guidewire 10 in its current position. A working device 1006, for example a balloon catheter, is the introduced over guidewire 10 and advanced thereover so that the proximal end of device 10 extends proximally beyond a proximal end of device 1006. Device 10 is then reconnected to connector 20 so that light is again emitted from the light emission portion of the distal end portion of device 10. Thus it can be visually confirmed, without radiography, that the distal end portion of the guidewire 10 remains properly in the frontal sinus 1036 as the working device 1006 is advanced toward ostium 1034 and the balloon of working device 1006 is extended across the ostium, FIG. 17D. The proper positioning of the working end (distal end portion) of working device 1006 can be visualized with the scope and/or fluoroscopy.

Once proper placement of the working device 1006 has been confirmed, working device 1006 is used to perform a diagnostic or therapeutic procedure. In this particular example, the procedure is dilatation of the frontal sinus ostium 1034 by expansion of the balloon thereagainst, to enlarge the opening of the ostium 1034. However, it will be appreciated that the present invention may also be used to dilate or modify any sinus ostium or other man-made or naturally occurring anatomical opening or passageway within the nose, paranasal sinuses, nasopharynx or adjacent areas. Further, other working tools may be inserted and used according to these same techniques. After the completion of the procedure, sinus guide 1002, guidewire 10 and working device 1006 are withdrawn and removed, completing the procedure, see FIG. 17E.

Figure 18:
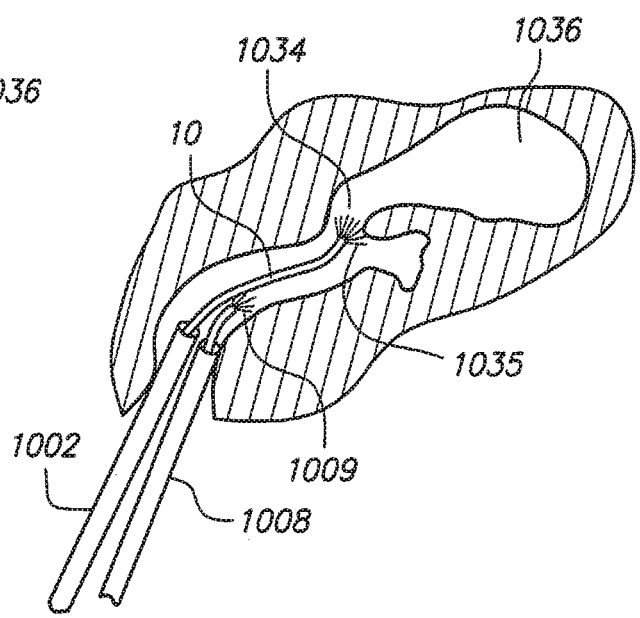
FIG. 18 illustrates a situation, like that described with regard to FIG. 3, where a scope has been inserted as far as possible without causing significant trauma to the patient. Additionally.

Illuminating guidewire device 10 can also be used to facilitate visualization and placement of the sinus guide 1002 in the procedure described above with regard to FIGS. 17A-17E, or in another procedure in which a sinus guide, guide catheter or guide tube is placed in the sinus pathways. FIG. 18 illustrates a situation, like that described above with regard to FIG. 3, where scope 1008 has been inserted as far as possible without causing significant trauma to the patient. The range of visibility in this case does not extend all the way to ostium 1034, as indicated schematically by the rays 1009 shown extending distally from scope 1008. In this case, adequate visualization of sinus guide 1002 by scope 1008 is possible only up to the extent of the rays 1009 shown. Thus, if sinus guide 1002 is flexible enough to be advanced more closely to ostium 1034, then adequate visualization of this movement would not be possible via scope 1008. That is, if sinus guide 1002 is physically capable of being extended further distally to place the distal end thereof at the approach to ostium 1034, scope 1008 would not be capable of adequately visualizing this. However, by inserting illuminating guidewire through sinus guide 1002 as shown in FIG. 18, additionally illumination can be provided distally of the illuminating range of scope 1008. This additional illumination can be received by scope 1008 to enable visualization up to the illumination portion of device 10 and potentially even extending to illumination range of device 10, as long as there is a straight pathway of the field of view. Thus, advancement of the sinus guide 1002 can be visualized further distally by the scope 1008 using this technique, and potentially all the way up to the ostium 1034.

Additionally, this technique can be used to visualize placement of the guidewire 10 up to and into the desired ostium 1034. Alternatively, this can be carried out without the sinus guide 1002, wherein the guidewire 10 is inserted and the scope 1008 can be used to visualize placement of guidewire 10 into the target ostium with the assistance of the light emitted by the scope 1008 in addition to the light emitted by guidewire 10.

In any of these procedures where a scope 1008 is used for visualization and an illuminating guidewire is inserted, some transillumination of the target sinus may occur from the light emitted by the scope 1008 alone. However, this transillumination will be diffuse and show a rather dim, large area of transillumination on the patient's skin. When the illumination guidewire is inserted and advanced, as noted earlier, a smaller, brighter transillumination spot will be visible when the illuminating portion of the guidewire has entered the sinus. Additionally, even before entering the sinus, the light emitted from the guidewire will produce a moving transillumination spot at guidewire 10 is advance, which also helps distinguish the location of the distal portion of the guidewire, relative to any diffuse transillumination produced by the scope light.

If the guidewire 10 is advanced into an ostium other than the target ostium (e.g., ostium 1035 shown in FIG. 18), this may be possible to be viewed by scope 1008, depending upon the line of sight. However, even if it is not, the transillumination resulting from entrance into a different sinus than the target sinus will be evident by the different location on the patient's face. Also, in the example shown, guidewire 10 would not be able to be advanced very far through ostium 135 before it was diverted and curled by the relatively small sinus space that ostium 135 leads into. Thus, by tracking the movement of the illumination spot produced by guidewire 10, the surgeon could confirm that guidewire 10 was misplaced as the guidewire would be diverted by a much smaller space then that characterized by the target frontal sinus 1036.

Thus, by using an illuminating guidewire device 10 in the methods as described above, the use of fluoroscopy or other X-ray visualization can be reduced is not required to confirm proper placement of the guidewire in some cases.

Similar procedures may be carried out in other sinuses. For example, a similar procedure to that described above with regard to FIGS. 17A-17E may be carried out to open or expand an opening of an ostium leading to a maxillary sinus. In this case, when illuminating guidewire device 10 passes through the ostium that opens to the target maxillary sinus and enters the maxillary sinus, a relatively bright, relatively small, defined transillumination spot can be observed to move across the cheek region of the patient. As guidewire 10 is advance further distally along the maxillary sinus, the maxillary sinus typically tends to track in an inferior direction relative to the skull, and the bottom wall of the maxillary sinus is very close to the palate of the patient. Therefore as the illuminating portion of guidewire approaches and/or touches the bottom wall of the maxillary sinus, a transillumination spot can be observed on the roof of the patient's mouth by looking into the mouth of the patient. At the same time, the transillumination spot on the cheek that was caused by the guidewire will diminish, or not be visible at all at this time. This viewability on the roof of the mouth is further confirmation that the guidewire has entered the maxillary sinus. Movement of the transillumination spot on the roof of the mouth can also be observed as the guidewire 10 is advanced and/or retracted.

Figure 19:
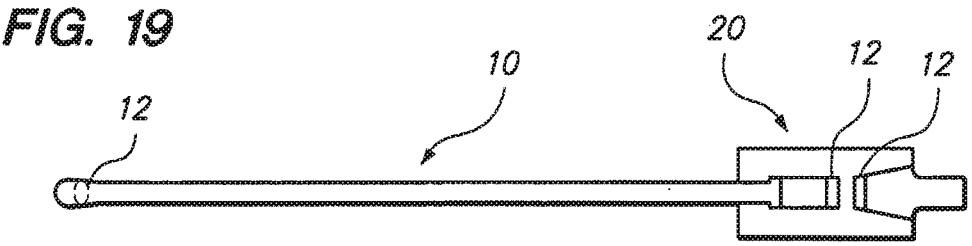
FIG. 19 illustrates non-limiting examples of where one or more filters may be placed in an illuminating guidewire device.

It is further noted that some wavelengths of light may be more effective in producing the transillumination effects described herein, for the purpose of locating the position of the guidewire. In this regard, particular wavelengths of visible light can be selected for this purpose. Alternatively, or in addition, infrared wavelengths may be particularly effective. In this regard, guidewires that employ illuminating fibers may be provided with a filter 12 to define the color/wavelength of the light emitted by device 10. As schematically shown in FIG. 19, filter 12 may be provided distally of the illumination fibers, such as at the distal tip of device 10, proximally of the illumination fibers, such as at the proximal end of device 10, or in the light pathway at a location within connector 20, for example. Multiple filters may be placed at one or more of these locations. For devices 10 that employ an LED light emitting component, different color LEDs may be employed to emit different wavelengths of light. For devices 10 that employ laser fibers, different types of lasers may be used that emit different wavelengths of light.

Figure 20A:
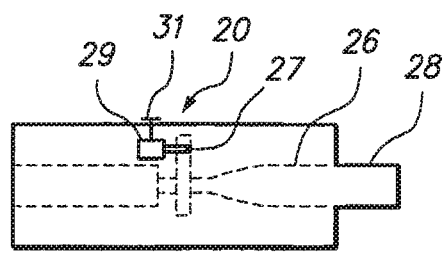
FIG. 20A schematically illustrates a connector having a rotating shutter rotatably mounted therein.
Figure 20B:
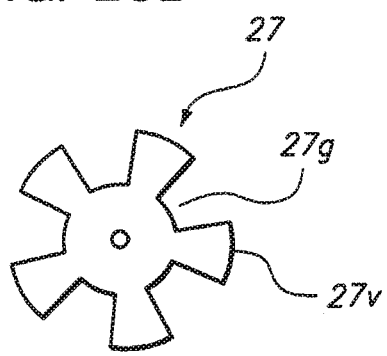
FIG. 20B is an illustration of a plan view of the shutter of FIG. 20A.

Another optional feature that guidewire 10 may be provided with is the ability to emit strobed, flashing or flickering light. The transillumination produced by a flashing light can be further distinguished from diffuse transillumination produced by other light sources, such as endoscopes, for example, since the transillumination produced by the guidewire 10 in this case will flicker or vary in intensity between bright and dim. To produce this type of light, either a light source having strobing capability could be connected to the device 10, or connector 20 may be provided with this capability. When using a laser light source or an LED as the light emitter, as described in embodiments above, a blinking or strobing effect can be electronically generated according to techniques known in the electronics and lighting arts. FIG. 20A schematically illustrates a connector 20 having a rotating shutter 27 rotatably mounted therein so that the vanes 27v and gaps 27g between the vanes (see plane view in FIG. 20B) become successively aligned with the light pathway through the connector 20 to alternate emission and blocking of light transmission out of the connector 20 and ultimately through device 10 when a device 10 is connected thereto. Shutter 27 can be powered by a motor 29 that is either battery powered or connectable to an operating room power source, and motor can be operated by the user via actuator 31, which can be configured to turn the motor on and off, and optionally can be configured to vary the speed of rotation. Alternatively, shutter can be configured so that vanes 27v extend through a slot in connector 20 whereby a user can manually rotate the shutter to cause the light emitted from device 10 to flicker.

Figure 21:
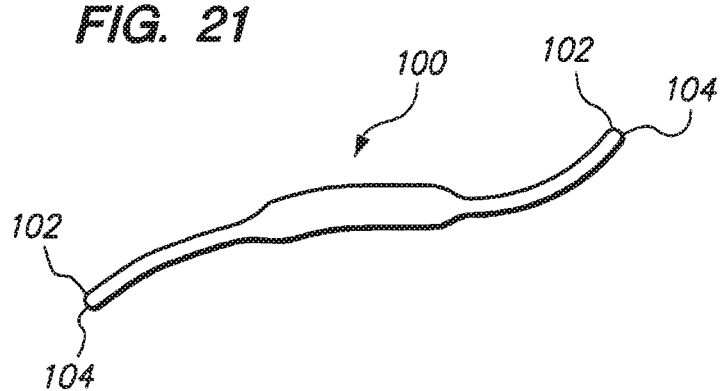
FIG. 21 shows a frontal ostium seeker instrument that can be used to access a sinus ostium.

Other instruments that are designed to be inserted into a sinus, or at least to be positioned at the ostium of a sinus can also be provided with illumination capability according to any or all of the features described above with regard to illumination guidewires. FIG. 21 shows a frontal ostium seeker 100 instrument that can be used to access a sinus ostium. For example, seeker 100 may be provided with a length of about 175 mm to about 250 mm (about 208 mm in the example shown) and a ball tip at one or both ends of the instrument. In FIG. 21, seeker 100 is also provided with a light emitter 104 at one or both ends of the device 100 that can be used to locate an end of device 100 as it is being advanced to seek an ostium, by the transillumination effects as discussed above. Light emitters 104 may be provided by LED, light illumination fibers or laser illumination fibers, for example. One or both end portions of the instrument may include a light fiber bundle or electrical wires for connection to a light source or power source in a manner as described above.

Figure 22:
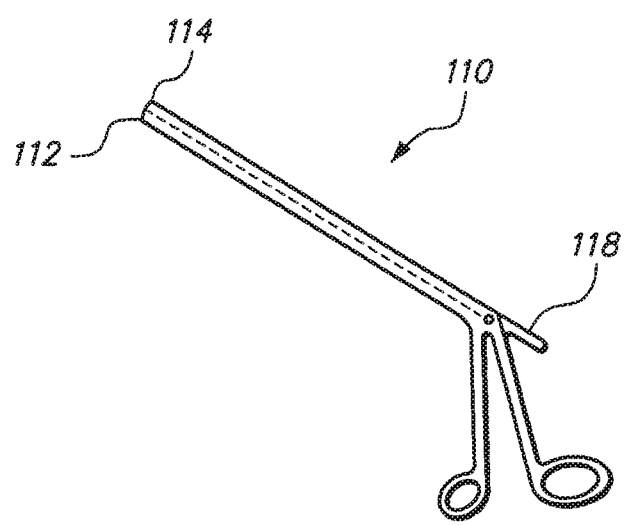
FIG. 22 shows a suction sinus instrument that is configured to evacuate blood and/or other fluids from a target surgical site, such as the frontal sinus.

FIG. 22 shows a suction sinus instrument 110 that is configured to evacuate blood and/or other fluids from a target surgical site, such as the frontal sinus, sphenoid sinus or other sinus, to improve visibility of a surgical procedure. Instrument 110 includes an elongated shaft 116 with a distal end that opens to deliver suction via a suction lumen end 112. Additionally, a light emitter 114 is provided at the distal end of shaft 116, which may be an LED or one or more illumination fibers configured to transmit light in a manner as described above. Shaft 116 is configured and dimensioned to be inserted into the sinus passageways and sinuses. The proximal end portion of instrument 110 may include a light fiber bundle 118 or electrical wires for connection to a light source or power source in a manner as described above.

Figure 23:
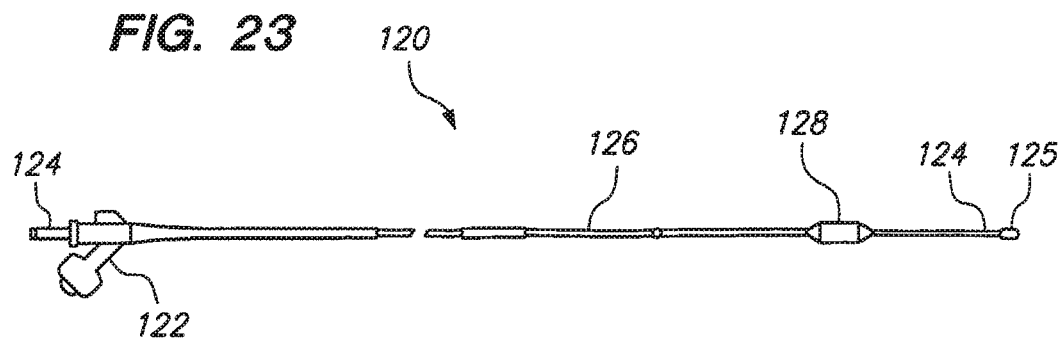
FIG. 23 shows an integrated wire dilatation catheter 120 that includes an elongate, flexible catheter shaft having a balloon mounted thereon.

FIG. 23 shows an integrated wire dilatation catheter 120 that includes an elongate, flexible catheter shaft 126 having a balloon 128 mounted thereon. A proximal Luer hub 122 is attached to the proximal end of the catheter shaft 126. An inflation device (not shown) may be attached to the Luer hub 122 and used to inflate and deflate the balloon 128. A non-removable, integrated guide member 124 extends out of and beyond the distal end of the catheter shaft 126. Guide member 124 can extend through the length of catheter shaft 126 and extend proximally thereof as shown in FIG. 23. The proximal end portion may be configured with a polished proximal end containing illumination fibers, as described previously, or may have one or more electrical wires extending proximally thereof for connection with an electrical power source to deliver electrical power to an LED, for example. A light emitter 125 may be provided at the distal tip of integrated guide member 124, as shown in FIG. 23 and may be one or more LEDs or one or more illumination fibers, according to any of the different embodiments described above. Alternatively, light emitter 125 may be provided proximally of the distal tip of guide member 124, in a manner like that described with regard to FIG. 10, for example. Further alternatively, guide member may not extend through the entire length of catheter 126 or may not extend proximally of balloon member 128 at all. In these examples, light emitter may be an LED, wherein wires can be threaded through or alongside of catheter 126 and into guide member 124 to connect with the LED. Further alternatively, if light emitter 125 comprises one or more illumination fibers, the illumination fibers may extend proximally of the proximal end of the guide member 124, and proximally through catheter 126 where they are not surrounded by an external sheath in a guidewire formation.

In one preferred embodiment for adult applications, balloon catheter 120 has an overall length of approximately 43.5 cm and its shaft 126 has an outer diameter of about 0.058 inches. Further details about integrated wire dilatation catheters that may be configured with a light emitter in a manner as described herein can be found in application Ser. No. 11/438,090 filed May 18, 2006 and titled "Catheters with Non-Removable Guide Members Useable for Treatment of Sinusitis," now U.S. Pat. No. 8,951,225, issued Feb. 10, 2015. Application Ser. No. 11/438,090, now U.S. Pat. No. 8,951,225, is hereby incorporated herein, in its entirety, by reference thereto.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:
1. A system comprising:
  (a) an illuminating guidewire having:
    (i) a proximal end,
    (ii) a distal end, and
    (iii) at least one illumination fiber extending between the proximal and distal ends,
    wherein the distal end is configured to be inserted through a nostril and into a paranasal sinus of a patient, wherein the at least one illumination fiber is configured to direct light distally through the distal end;
  (b) a dilation catheter having an expandable dilator, wherein the expandable dilator is movable over the illuminating guidewire for positioning within an opening to the paranasal sinus, wherein the expandable dilator is selectively transitionable between an unexpanded state and an expanded state for expanding the opening; and
  (c) a connector configured to releasably couple the proximal end of the illuminating guidewire with a light source, wherein the connector is configured to manipulate light transmitted distally therethrough from the light source to the illuminating guidewire, wherein the connector includes a tapering light channel configured to focus light received from the light source and communicate the focused light distally to the at least one illumination fiber of the illuminating guidewire.
2. The system of claim 1, wherein a distal end diameter of the tapering light channel is smaller than a proximal end diameter of the tapering light channel, wherein the distal end diameter is equal to or greater than an inner diameter of the at least one illumination fiber.

3. The system of claim 1, wherein a distal end diameter of the tapering light channel is smaller than a proximal end diameter of the tapering light channel, wherein the distal end diameter is equal to or greater than an outer diameter of the proximal end of the illumination guidewire.

4. The system of claim 1, wherein the connector includes a proximal portion and a distal portion, wherein the tapering light channel is arranged within the proximal portion and tapers distally toward the distal portion.

5. The system of claim 4, wherein the connector further includes a guidewire channel arranged within the distal portion, wherein the guidewire channel communicates proximally with the tapering light channel and is configured to releasably receive the proximal end of the illuminating guidewire.

6. The system of claim 5, wherein the connector further includes a locking mechanism configured to releasably retain the proximal end of the illuminating guidewire within the guidewire channel.

7. The system of claim 6, wherein the locking mechanism further comprises a locking arm, wherein the locking arm includes a first portion configured to extend into the guidewire channel and a second portion configured to extend outwardly from an exterior of the connector, wherein the second portion is retractable to transition the locking arm between a locked position and an unlocked position, wherein in the locked position the locking mechanism is operable to retain the proximal end of the illuminating guidewire within the guidewire channel, wherein in the unlocked position the locking mechanism is operable to permit release of the proximal end of the illuminating guidewire from within the guidewire channel.

8. The system of claim 1, wherein the connector includes a main body and a light post coupled to the main body and extending proximally therefrom, wherein at least a portion of the tapering light channel extends through the light post.

9. The system of claim 8, wherein an outer surface of the light post includes an annular groove configured to facilitate relative rotation between the connector and the light source.

10. The system of claim 1, wherein the system is configured to emit flashes of light through the distal end of the illuminating guidewire.

11. The system of claim 10, wherein the connector includes a light channel configured to communicate light from the light source to the at least one illumination fiber of the illuminating guidewire, wherein the connector further includes a movable member configured to interrupt light passing distally through the light channel to thereby produce a flashing light effect at the distal end of the illuminating guidewire.

12. The system of claim 11, wherein the movable member includes a rotating shutter having at least one vane and at least one gap, wherein the at least one gap is configured to permit transmission of light distally through the light channel to the illuminating guidewire, and the at least one vane is configured to block transmission of light distally through the light channel to the illuminating guidewire, wherein the rotating shutter is configured to rotate to successively align the at least one vane and the at least one gap with the light channel to thereby produce the flashing light effect at the distal end of the illuminating guidewire.

13. The system of claim 12, further comprising a motor configured to power rotation of the rotating shutter within the connector.

14. The system of claim 1, further comprising a xenon light source.

15. The system of claim 1, further comprising a guide device having a lumen configured to receive the illuminating guidewire therethrough, wherein the expandable dilator is configured to pass through the lumen.

16. The system of claim 15, wherein the expandable dilator is configured to remain in the unexpanded state when positioned distally of the guide device.

17. The system of claim 1, wherein the illuminating guidewire has a length sufficient to extend from a proximal location exterior to the patient to a distal location within the patient's paranasal sinus.

18. A system comprising:
(a) an illuminating guidewire having:
  (i) a proximal end,
  (ii) a distal end, and
  (iii) at least one illumination fiber extending between the proximal and distal ends,
  wherein the distal end is configured to be inserted through a nostril and into a paranasal sinus of a patient, wherein the at least one illumination fiber is configured to direct light distally through the distal end; and
(b) a connector configured to releasably couple the proximal end of the illuminating guidewire with a light source, wherein the connector comprises:
  (i) a proximal portion having a tapering light channel, and
  (ii) a distal portion having a guidewire channel,
  wherein the guidewire channel communicates with the tapering light channel and is configured to receive the proximal end of the illuminating guidewire,
  wherein the tapering light channel tapers distally and is configured to focus light received from the light source and communicate the focused light distally to the at least one illumination fiber of the illuminating guidewire.

19. The system of claim 18, wherein the connector further includes a movable member configured to generate a flashing effect of light emitted through the distal end of the illuminating guidewire.

20. A system comprising:
(a) an illuminating guidewire having:
  (i) a proximal end portion,
  (ii) a distal end portion, and
  (iii) a plurality of illumination fibers extending between the proximal and distal end portions,
  wherein the distal end portion is configured to be inserted through a nostril and into a paranasal sinus of a patient, wherein the illumination fibers are configured to communicate light from the proximal end portion to the distal end portion, wherein the distal end portion is configured to emit the light;
(b) a guide device having a lumen configured to receive the illuminating guidewire;
(c) a dilation catheter having an expandable dilator that is selectively transitionable between an unexpanded state and an expanded state, wherein the expandable dilator is movable over the illuminating guidewire for positioning within an opening to the paranasal sinus, wherein the expandable dilator is configured to remain in the unexpanded state when positioned distally of the guide device until expansion is triggered by a user to thereby expand the opening to the paranasal sinus; and
(d) a connector configured to releasably couple the proximal end portion of the illuminating guidewire with a light source, wherein the connector includes a tapering light channel configured to transition light received from the light source into at least one illumination fiber of the illuminating guidewire.

* * * * *